United States Patent
Su'etsugu et al.

(10) Patent No.: US 11,685,940 B2
(45) Date of Patent: Jun. 27, 2023

(54) METHOD OF REPLICATING OR AMPLIFYING CIRCULAR DNA

(71) Applicant: OriCiro Genomics, Inc., Tokyo (JP)

(72) Inventors: Masayuki Su'etsugu, Tokyo (JP); Seia Nara, Tokyo (JP)

(73) Assignee: Moderna Enzymatics Co., Ltd., Tokyo (JP)

( * ) Notice: Subject to any disclaimer, the term of this patent is extended or adjusted under 35 U.S.C. 154(b) by 217 days.

(21) Appl. No.: 16/489,428

(22) PCT Filed: Feb. 28, 2018

(86) PCT No.: PCT/JP2018/007485
§ 371 (c)(1),
(2) Date: Aug. 28, 2019

(87) PCT Pub. No.: WO2018/159669
PCT Pub. Date: Sep. 7, 2018

(65) Prior Publication Data
US 2020/0115727 A1    Apr. 16, 2020

(30) Foreign Application Priority Data
Feb. 28, 2017    (JP) ................... 2017-037489

(51) Int. Cl.
C12Q 1/68    (2018.01)
C12P 19/34    (2006.01)
C12N 15/10    (2006.01)

(52) U.S. Cl.
CPC .............. *C12P 19/34* (2013.01); *C12N 15/10* (2013.01)

(58) Field of Classification Search
CPC ....................................................... C12Q 1/68
(Continued)

(56) References Cited

U.S. PATENT DOCUMENTS 6,506,581 B1 *  1/2003  Fleischmann ........... A61P 31/12
                                                          435/69.1
10,301,672 B2   5/2019  Su'etsugu et al.
(Continued)

FOREIGN PATENT DOCUMENTS

EP    1916311 A1    4/2008
EP    3222717 A1    9/2017
(Continued)

OTHER PUBLICATIONS

Hiasa, H., et al., Topoisomerase IV can supportoriC DNA replication in vitro, J. Biol. Chem., 1994, vol. 269, No. 23, pp. 16371-16375, ISSN 0021-9258.*
(Continued)

*Primary Examiner* — Aaron A Priest
(74) *Attorney, Agent, or Firm* — Sunit Talapatra; Foley & Lardner LLP

(57) ABSTRACT

Provided is a method capable of replicating or amplifying circular DNA, and particularly, long-chain circular DNA, in a cell-free system. Specifically, provided is a method for suppressing generation of a DNA multimer as a by-product, when circular DNA having a replication origin sequence (origin of chromosome (oriC)) is replicated or amplified by using the following enzyme groups:
 (1) a first enzyme group that catalyzes replication of circular DNA;
 (2) a second enzyme group that catalyzes an Okazaki fragment maturation and synthesizes two sister circular DNAs constituting a catenane; and
 (3) a third enzyme group that catalyzes a separation of two sister circular DNAs.
Moreover, also provided is a method comprising introducing oriC into circular DNA by using a transposon.

8 Claims, 19 Drawing Sheets

Specification includes a Sequence Listing.

(58) Field of Classification Search
USPC .......................................................... 435/6
See application file for complete search history.

(56) References Cited

U.S. PATENT DOCUMENTS

| | | |
|---|---|---|
| 2010/0028862 A1 | 2/2010 | Jarvis et al. |
| 2017/0321263 A1 | 11/2017 | Su'Etsugu et al. |
| 2019/0249236 A1 | 8/2019 | Su'Etsugu et al. |
| 2019/0276883 A1 | 9/2019 | Su'etsugu et al. |

FOREIGN PATENT DOCUMENTS

| | | |
|---|---|---|
| JP | 2005229950 A | 9/2005 |
| JP | 2008-161182 A | 7/2008 |
| JP | 2012-501173 A | 1/2012 |
| WO | 199523875 A1 | 9/1995 |
| WO | 200078977 A1 | 12/2000 |
| WO | 2010026099 A1 | 3/2010 |
| WO | 2016080424 A1 | 5/2016 |

OTHER PUBLICATIONS

Beattie etal, A Replisome's journey through the bacterial chromosome, Front Microbiol. Jun. 5, 2015;6:562. doi: 10.3389/fmicb.2015.00562. eCollection 2015.*

Kuzminov, Recombinational repair of DNA damage in *Escherichia coli* and bacteriophage lambda, Microbiol Mol Biol Rev. Dec. 1999;63(4):751-813.*

Baileyetai, Termination of DNA replication forks: "Breaking up is hard to do", Nucleus. 2015;6(3):187-96. doi: 10.1080/19491034.2015.1035843. Epub Apr. 2, 2015.*

Hiasa etal, Topoisomerase IV can supportoriC DNA replication in vitro, J Biol Chem. Jun. 10, 1994;269(23):16371-5.*

Suski et al., Resolution of Converging Replication Forks by RecQand Topoisomerase III, Mol Cell. Author manuscript; available in PMC Jun. 20, 2009. Published in final edited form as: Mol Cell. Jun. 20, 2008; 30(6): 779-789. doi: 10.1016/j.molcel.2008.04.020.*

Hiasa, H. et al. (1994). "Primase Couples Leading- and Lagging-strand DNA." The Journal of Biological Chemistry 269(8): 6058-6063.

Bailey et al. (2015) "Termination of DNA Replication Forks: Breaking up is hard to do", Nucleus, 6(3): 187-196.

C.Y.Ip et al. (Dec. 1, 2003) "Decatenation of DNA Circles by FtsK-dependent Xer site-specific Recombination", The EMBO Journal, , 22(23): 6399-6407.

Chao, R. et al. (2015). "Recent advances in DNA assembly technologies." FEMS Yeast Research 15:1-9.

Chen, Z. et al. (Dec. 1, 1998). "Amplification of closed circular DNA in vitro," Nucleic Acids Res 26 (23):1126-1127.

Extended European Search Report dated Dec. 16, 2019 for European Application No. 17799415.9, filed on May 17, 2017. 5 pages.

Extended European Search Report dated Mar. 27, 2018, for EP Application No. 15860324.1, 9 pages.

Fakrrudin, M. et al. (2013). "Nucleic acid amplification: Alternative methods of polymerase chain reaction." Journal of Pharmacy and Bioallied Sciences 5(4): 245-252.

Funnell, B. et al. (Apr. 25, 1986). "Complete enzymatic replication of plasmids containing the origin of the *Escherichia coli* chromosome," J Biol Chem 261(12):5616-5624.

Gusev, Y. et al. (2001). "Rolling circle amplification: A new approach to increase sensitivity for immunohistochemistry and flow cytometry." American Journal of Pathology 159(1):63-69.

Hiasa, H. et al. (1994). "Topoisomerase IV can support OriC DNA replication in vitro." The Journal of Biological Chemistry 269(23):16371-16375.

Hiasa, H. et al. (1994). "Tus prevents overreplication of oriC plasmid DNA." The Journal of Biological Chemistry 269 (43):26959-26968.

Hiasa, H. et al. (Jan. 21, 1994). "Decatenating activity of *Escherichia coli* DNA gyrase and topoisomerases I and III during oriC and pBR322 DNA replication in vitro," The Journal of Biological Chemistry 269(3):2093-2099.

Hiasa, H. et al. (1994). "Topoisomerase III, but not topoisomerase I, can support nascent chain elongation during theta-type DNA replication." The Journal of Biological Chemistry 269(51):32655-32659.

International Search Report dated May 29, 2018 for International Application No. PCT/JP2018/007485, filed on Feb. 28, 2018. 2 pages.

International Search Report dated Aug. 15, 2017 for International Application No. PCT/JP2017/018472, filed May 17, 2017. 5 pages.

International Search Report dated Feb. 16, 2016 for International Application No. PCT/JP2015/082356, filed Nov. 18, 2015. 2 pages.

Kaguni, J. et al. (1984). "Replication initiated at the origin (OriC) of the *E. coli* chromosome reconstituted with purified enzymes." Cell 38:183-190.

Peng, H. et al. (1993). "Decatenation activity of topoisomerase IV during oriC and pBR322 DNA replication in vitro." Proceedings of the National Academy of Sciences USA 90:8571-8575.

Su'Etsugu, M. et al. (Nov. 16, 2017). "Exponential propagation of large circular DNA by reconstitution of a chromosome-replication cycle," Nucleic Acids Res 45(20):11525-11534.

Suski, C. et al. (2008). "Resolution of converging replication forks by RecQ and topoisomerase III." Molecular Cell 30 (6):779-789.

Tsuge, K. et al. (2003). "One step assembly of multiple DNA fragments with a designed order and orientation in Bacillus subtillis plasmid." Nucleic Acids Research vol. 31, No. 21. 8 pages.

Kelman et al. (1995) "DNA Polymerase III Holoenzyme: Structure and Function of a Chromosomal Replicating Machine", Annual Review of Biochemistry, 64:171-200.

Wowor et al. (Jun. 2010) "Thermodynamics of the DNA Structural Selectivity of the Pol I Polymerases from *Escherichia coli* and Thermus and aquaticus", Biophysical Journal, 98:3015-3024.

Fuller et al, (1981) " Enzymatic replication of the origin of the *Escherichia coli* chromosome", Department of Biochemistry, 78(12):7370-7374.

Schauzu et al, (1987) "Transcripts within the replication origin oriC, of *Escherichia coli* ", Max-Planck-Institut fur Mokeulare Genetik, 15(6):2479-2497.

* cited by examiner (a)

(b)

METHOD OF REPLICATING OR AMPLIFYING CIRCULAR DNA

CROSS-REFERENCE TO RELATED APPLICATIONS

This application is a national stage entry, filed under 35 U.S.C. § 371, of International Application No. PCT/JP2018/007485, filed on Feb. 28, 2018, which claims the benefit of priority from Japanese Patent Application No. 2017-037489, filed on Feb. 28, 2017, the entire contents of which are incorporated herein by reference in their entirety.

SEQUENCE LISTING

The instant application contains a Sequence Listing which has been submitted via EFS-Web. The content of the text file named "Sequence_Listing.txt", which was created on Feb. 27, 2018 and is 13,842 bytes in size, is hereby incorporated by reference in its entirety.

TECHNICAL FIELD

The present invention relates to a method for replicating or amplifying circular DNA. More specifically, the present invention relates to a method capable of efficiently replicating or amplifying circular DNA in a cell-free system. The present invention also relates to a nucleic acid capable of being utilized as a functional cassette for preparing circular DNA.

BACKGROUND ART

The DNA cloning technology on which biotechnological development was based is a technique for amplifying circular DNA that had been prepared by cutting and pasting DNA fragments as plasmid in cells of E. coli, etc. A use of a DNA cloning technology that uses cells to amplify circular DNA necessitates troublesome procedures such as cell cultivation, extraction/purification of amplified products and the like. Also, the environment for experimenting such DNA cloning is limited, since it is necessary to prepare genetically modified organisms to perform DNA cloning that uses cells.

A common method used for amplifying DNA in vitro is polymerase chain reaction (PCR). However, an in vitro DNA amplification using PCR does not allow circular DNA to be amplified as it is. In vitro amplification methods of circular DNA include the rolling circle amplification (RCA) (NPL 1, PTL 1, PTL 2, PTL 3). However, if circular DNA is to be amplified using the rolling circle amplification, a primer specific to the target DNA would need to be designed each time. Furthermore, the amplification product that directly results from the rolling circle amplification is a linear DNA, so it would be necessary to perform an additional cyclization step to cyclize the obtained amplification product, such as incubating with a recombination enzyme. Another reported method is a method of obtaining a monomer replication product by replicating a minichromosome of E. coli (oriC circular DNA) and then separating it to obtain a monomeric circular replication product has been reported (NPLs 2 to 5). However, with regard to the reaction conditions applied in these publications, it has been experimentally demonstrated that the replication efficiency of circular DNA molecules is only approximately 15 to 40% of the added template DNA, and thus that the amplified amount does not reach even double (NPLs 3 to 6). Furthermore, the size of circular DNA used as a template in these publications is only less than 10 kbp.

As shown above, amplification of circular DNA using the conventional in vitro DNA amplification was disadvantageous in that it required primers to be bonded with the template DNA, produced linear DNA as the amplification product, and limited the size of DNA that can be amplified to within a few kbp. Still further, there has been a problem that, when a circular amplification product intends to be produced using an Escherichia coli minichromosome replication system, template circular DNA cannot be amplified even to double.

CITATION LIST

Patent Literature

PTL 1: Japanese unexamined patent publication No. 2005-229950
PTL 2: Japanese unexamined patent publication No. 2008-161182
PTL 3 Japanese unexamined patent publication No. 2012-501173

Non Patent Literature

NPL 1: Fakruddin M et al., J Pharm Bioallied Sci. 2013, 5: 245-252
NPL 2: Peng H & Marians K J. PNAS. 1993, 90: 8571-8575
NPL 3: Hiasa H & Marians K J. J Biol Chem. 1994, 269: 32655-32659
NPL 4: Funnell B et al., J Biol Chem. 1986, 261: 5616-5624
NPL 5: Hiasa H et al., J Biol Chem. 1994, 269: 2093-2099
NPL 6: Hiasa H & Marians K J. J Biol Chem. 1994, 269: 26959-26968

SUMMARY OF INVENTION

Technical Problem

The present invention provides a method capable of efficiently replicating or amplifying circular DNA in a cell-free system. The present invention also provides a nucleic acid capable of being utilized as a functional cassette for preparing circular DNA.

Solution to Problem

The present inventors performed extensive studies to solve the above problem and found that, when circular DNA having a replication origin sequence (origin of chromosome (oriC)) is replicated or amplified by using the following enzyme groups:
(1) a first enzyme group that catalyzes replication of circular DNA;
(2) a second enzyme group that catalyzes an Okazaki fragment maturation and synthesizes two sister circular DNAs constituting a catenane; and
(3) a third enzyme group that catalyzes a separation of two sister circular DNAs, generation of a DNA multimer as a by-product can be suppressed by utilizing a replication termination mechanism using ter-Tus, and/or a DNA multimer separation mechanism using a site-specific recombination system such as dif-XerCD. Moreover, the present inventors also found that even in a case where circular DNA comprising no oriC is present in an extremely low concentration, the circular DNA can be replicated or amplified by introducing oriC into the circular DNA, using a transposon.

In the present description, the reaction of replicating or amplifying circular DNA by using the above described enzyme groups (1), (2), and (3) is referred to as "RCR (replication-cycle reaction)" in some cases.

Furthermore, in the present description, the term "DNA multimer" means multimeric DNA generated upon replication or amplification of circular DNA. Herein, the multimeric DNA means that the concerned DNA is multimerized, when the circular DNA used as a template is defined as a monomer. In the present description, the DNA multimer is simply referred to as a "multimer" at times.

In other words, the present application encompasses the following aspect without being limited thereby.

[1] A method for replicating circular DNA in a cell-free system, comprising the following steps:

(1) forming a reaction mixture of circular DNA as a template with a reaction solution comprising:

a first enzyme group that catalyzes replication of circular DNA, a second enzyme group that catalyzes an Okazaki fragment maturation and synthesizes two sister circular DNAs constituting a catenane, and a third enzyme group that catalyzes a separation of two sister circular DNAs; and (2) reacting the reaction mixture formed in step (1), wherein the circular DNA includes a replication origin sequence (origin of chromosome (oriC)) that can bind to an enzyme having DnaA activity, and further includes a pair of ter sequences that are each inserted outward with respect to oriC, and/or a nucleotide sequence recognized by a DNA multimer separation enzyme, wherein when the circular DNA has the ter sequences, the reaction solution in step (1) further comprises a protein having an activity of inhibiting replication by binding to the ter sequences, and when the circular DNA has the nucleotide sequence recognized by a DNA multimer separation enzyme, the reaction solution in step (1) further comprises the DNA multimer separation enzyme.

[2] The method according to the above [1], wherein the DNA multimer separation enzyme is Cre or XerCD.

[3] A method for replicating circular DNA in a cell-free system, comprising the following steps:

(1) forming a reaction mixture of circular DNA as a template with a reaction solution comprising:

a first enzyme group that catalyzes replication of circular DNA, a second enzyme group that catalyzes an Okazaki fragment maturation and synthesizes two sister circular DNAs constituting a catenane, and a third enzyme group that catalyzes a separation of two sister circular DNAs; and (2) reacting the reaction mixture formed in step (1), wherein the circular DNA includes a replication origin sequence (origin of chromosome (oriC)) that can bind to an enzyme having DnaA activity, and further includes a pair of ter sequences that are each inserted outward with respect to oriC, and/or a nucleotide sequence recognized by XerCD, wherein when the circular DNA has the ter sequences, the reaction solution in step (1) further comprises a protein having an activity of inhibiting replication by binding to the ter sequences, and when the circular DNA has the nucleotide sequence recognized by XerCD, the reaction solution in step (1) further comprises a XerCD protein.

[4] The method according to any one of the above [1] to [3], wherein the pair of ter sequences that are each inserted outward with respect to oriC comprises: a sequence comprising any one of sequences shown in SEQ ID NOS: 1 to 14 which is inserted as one ter sequence into the 5'-terminal side of oriC; and a sequence comprising a complementary sequence to any one of sequences shown in SEQ ID NOS: 1 to 14 which is inserted as the other ter sequence into the 3'-terminal side of oriC.

[5] The method according to any one of the above [1] to [4], wherein the protein having an activity of inhibiting replication by binding to the ter sequences is a Tus protein or an RTP protein.

[6] The method according to the above [2] or [3], wherein the nucleotide sequence recognized by XerCD is a sequence comprising any one of sequences shown in SEQ ID NOS: 15 to 24, or a complementary sequence thereto.

[7] The method according to the above [2], wherein nucleotide sequence recognized by Cre is a sequence comprising any one of sequences shown in SEQ ID NOS: 30 to 35, or a complementary sequence thereto.

[8] A nucleic acid, which is linear DNA having a length of 273 bp to 2.0 kb, and comprises oriC, and a pair of ter sequences that are each inserted outward with respect to the oriC and/or a nucleotide sequence recognized by a DNA multimer separation enzyme.

[9] A nucleic acid, which is linear DNA having a length of 273 bp to 2.0 kb, and comprises oriC, and a pair of ter sequences that are each inserted outward with respect to the oriC and/or a nucleotide sequence recognized by XerCD.

[10] A method for replicating circular DNA in a cell-free system, comprising the following steps:

(1) prepare circular DNA comprising oriC by:

adding an oriC transposon and transposase into a buffer to form an oriC transposome, wherein the oriC transposon is linear DNA comprising a replication origin sequence (origin of chromosome (oriC)) that can bind to an enzyme having DnaA activity, and comprising outside end (OE) sequences at both termini thereof; and reacting the oriC transposome with circular DNA comprising no oriC in a buffer to carry out a transfer reaction, (2) forming a reaction mixture of the circular DNA comprising oriC obtained in step (1) with a reaction solution comprising:

a first enzyme group that catalyzes replication of circular DNA, a second enzyme group that catalyzes an Okazaki fragment maturation and synthesizes two sister circular DNAs constituting a catenane, and a third enzyme group that catalyzes a separation of two sister circular DNAs; and (3) reacting the reaction mixture formed in step (2).

[11] The method according to the above [10], wherein the OE sequence comprises the sequence shown in SEQ ID NO: 25 (5'-CTGTCTCTTATACACATCT-3') and a complementary sequence thereto, and the OE sequence comprising the sequence shown in SEQ ID NO: 25 is inserted into the 5'-terminus of the linear DNA in step (1), and the OE sequence comprising a complementary sequence to the sequence shown in SEQ ID NO: 25 is inserted into the 3'-terminus of the linear DNA.

[12] The method according to the above [10] or [11], wherein the circular DNA comprising oriC further comprises a pair of ter sequences that are each inserted outward with respect to oriC, and/or a nucleotide sequence recognized by a DNA multimer separation enzyme, wherein when the circular DNA has the ter sequences, the reaction solution in step (2) further comprises a protein having an activity of inhibiting replication by binding to the ter sequences, and when the circular DNA has the nucleotide sequence recognized by a DNA multimer separation enzyme, the reaction solution in step (2) further comprises the DNA multimer separation enzyme.

[13] The method according to the above [10] or [11], wherein the circular DNA comprising oriC further comprises a pair of ter sequences that are each inserted outward with respect to oriC, and/or a nucleotide sequence recognized by XerCD, wherein when the circular DNA has the ter sequences, the reaction solution in step (2) further comprises a protein having an activity of inhibiting replication by binding to the ter sequences, and when the circular DNA has the nucleotide sequence recognized by XerCD, the reaction solution in step (2) further comprises a XerCD protein.

[14] The method according to any one of the above [10] to [13], wherein the oriC transposon in step (1) further comprises a pair of ter sequences that are each inserted outward with respect to oriC, and/or a nucleotide sequence recognized by a DNA multimer separation enzyme, wherein when the linear DNA has the ter sequences, the reaction solution in step (2) further comprises a protein having an activity of inhibiting replication by binding to the ter sequences, and when the circular DNA has the nucleotide sequence recognized by a DNA multimer separation enzyme, the reaction solution in step (2) further comprises the DNA multimer separation enzyme.

[15] The method according to any one of the above [10] to [13], wherein the oriC transposon in step (1) further comprises a pair of ter sequences that are each inserted outward with respect to oriC, and/or a nucleotide sequence recognized by XerCD, wherein when the linear DNA has the ter sequences, the reaction solution in step (2) further comprises a protein having an activity of inhibiting replication by binding to the ter sequences, and when the circular DNA has the nucleotide sequence recognized by XerCD, the reaction solution in step (2) further comprises a XerCD protein.

[16] The method according to any one of the above [10] to [15], further comprising:

(4) removing the oriC transposon from the circular DNA replicated or amplified in the reaction product in step (3).

[17] A nucleic acid, which is linear DNA having a length of 311 bp to 2.0 kb, and comprises oriC, and a pair of ter sequences that are each inserted outward with respect to the oriC and/or a nucleotide sequence recognized by a DNA multimer separation enzyme, and also comprises outside end (OE) sequences at both termini thereof.

[18] A nucleic acid, which is linear DNA having a length of 311 bp to 2.0 kb, and comprises oriC, and a pair of ter sequences that are each inserted outward with respect to the oriC and/or a nucleotide sequence recognized by XerCD, and also comprises outside end (OE) sequences at both termini thereof.

[19] A kit for replicating circular DNA, comprising a combination of:

a first enzyme group that catalyzes replication of circular DNA;

a second enzyme group that catalyzes an Okazaki fragment maturation and synthesizes two sister circular DNAs constituting a catenane;

a third enzyme group that catalyzes a separation of two sister circular DNAs;

an oriC transposon, which is linear DNA comprising a replication origin sequence (origin of chromosome (oriC)) that can bind to an enzyme having DnaA activity, and comprising outside end (OE) sequences at both termini thereof; and transposase.

[20] The kit according to the above [19], wherein the oriC transposon further comprises a pair of ter sequences that are each inserted outward with respect to oriC, and/or a nucleotide sequence recognized by a DNA multimer separation enzyme.

[21] The kit according to the above [20], further comprising:

a protein having an activity of inhibiting replication by binding to the ter sequences; and/or a DNA multimer separation enzyme.

[22] The kit according to the above [19], wherein the oriC transposon further comprises a pair of ter sequences that are each inserted outward with respect to oriC, and/or a nucleotide sequence recognized by XerCD.

[23] The kit according to the above [22], further comprising: a protein having an activity of inhibiting replication by binding to the ter sequences; and/or a XerCD protein.

Advantageous Effects of Invention

According to the method of the present application, when circular DNA having a replication origin sequence (origin of chromosome (oriC)) is replicated or amplified by using the following enzyme groups:

(1) a first enzyme group that catalyzes replication of circular DNA;

(2) a second enzyme group that catalyzes an Okazaki fragment maturation and synthesizes two sister circular DNAs constituting a catenane; and (3) a third enzyme group that catalyzes a separation of two sister circular DNAs, generation of a DNA multimer as a by-product can be suppressed. Moreover, an extremely low concentration of circular DNA can be replicated or amplified by introducing oriC into the circular DNA by using a transposon. From these findings, a replication product or an amplification product can be efficiently obtained according to the method of the present application.

DESCRIPTION OF EMBODIMENTS

Figure 1:
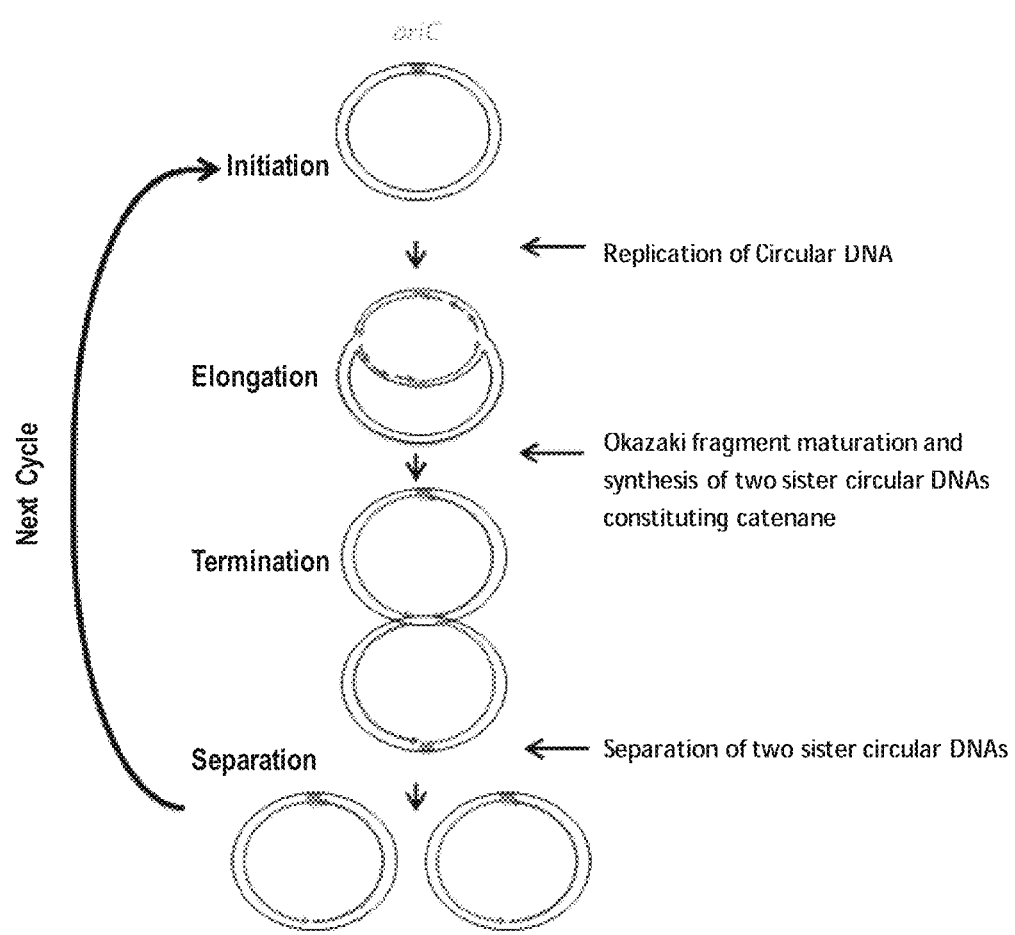
FIG. 1 shows a model of the replication cycle of circular DNA.

Hereafter, the present invention will be specifically described. However, the present invention is not limited to the following descriptions. The scientific terms and technical terms used with regard to the present invention have meanings, which are commonly understood by a person skilled in the art, unless otherwise specified in the present description.

<Circular DNA>

The circular DNA that is used as the template is preferably a double-strand. The circular DNA used as the template is not particularly limited as long as it includes a replication origin sequence (origin of chromosome (oriC)) that can bind to an enzyme having DnaA activity, and examples include natural circular DNA such as a circular chromosome of microorganisms, circular DNA created by ligating natural circular DNA that had been cut off by enzyme processing, etc. with another DNA fragment and cyclizing the ligated product, circular DNA created by performing a circularization treatment on DNA existing in a linear state in the nature, and circular DNA that had been artificially synthesized altogether. With regards to replication origin sequences (oriC) that can bind to an enzyme having DnaA activity (may be described hereinafter, simply as "replication origin sequence" or "oriC"), publicly known replication origin sequences existing in bacterium, such as *E. coli, Bacillus subtilis*, etc., may be obtained from a public database such as NCBI (http://www.ncbi.nlm.nih.gov/). Or else, the replication origin sequence may be obtained by cloning a DNA fragment that can bind to an enzyme having DnaA activity and analyzing its base sequence.

The circular DNA that is to be used as a template in the present invention may be circular DNA containing a replication origin sequence from the beginning, or circular DNA originally lacking a replication origin sequence but later incorporating a replication origin sequence.

As a method of preparing circular DNA used as a template by introducing a replication origin sequence into circular DNA originally lacking a replication origin sequence, a means known to a person skilled in the art can be applied. In one embodiment, introduction of a replication origin sequence into circular DNA lacking such a replication origin sequence may be carried out by adding transposon DNA comprising a replication origin sequence, which is a 5'-terminus-phosphorylated linear DNA comprising a replication origin sequence and also comprising outside end (OE) sequences at both termini thereof, and transposase into a buffer to form a transposome comprising a replication origin sequence, and then reacting the transposome comprising a replication origin sequence with the circular DNA lacking such a replication origin sequence in a buffer to carry out a transfer reaction.

The circular DNA that is used as a template in the present invention may include marker gene sequences that are resistant to drugs, such as kanamycin, ampicillin, tetracycline, etc. according to the purpose.

Furthermore, the circular DNA that is used as a template in the present invention may be in a purified state, or it may be in a form of a suspension of bacterial extraction including circular DNA. A single type of circular DNA may be used as a template, but it is also possible to use a mixture of several types of circular DNAs, such as a DNA library, in one test tube as a template.

There is no limit to the length of circular DNA used as a template in the present invention, and the length may be 1 kb (1,000 base length) or longer, 5 kb (5,000 base length) or longer, 8 kb (8,000 base length) or longer, 10 kb (10,000 base length) or longer, 50 kb (50,000 base length) or longer, 100 kb (100,000 base length) or longer, 200 kb (200,000 base length) or longer, 500 kb (500,000 base length) or longer, 1000 kb (1,000,000 base length) or longer, or 2000 kb (2,000,000 base length) or longer.

<First, Second and Third Enzyme Groups>

1. First Enzyme Group

In the present description, the first enzyme group means an enzyme group that catalyzes replication of circular DNA.

An example of a first enzyme group that catalyzes replication of circular DNA is an enzyme group set forth in Kaguni J M & Kornberg A. Cell. 1984, 38:183-90. Specifically, examples of the first enzyme group include one or more enzymes or enzyme group selected from a group consisting of an enzyme having DnaA activity, one or more types of nucleoid protein, an enzyme or enzyme group having DNA gyrase activity, single-strand binding protein (SSB), an enzyme having DnaB-type helicase activity, an enzyme having DNA helicase loader activity, an enzyme having DNA primase activity, an enzyme having DNA clamp activity, and an enzyme or enzyme group having DNA polymerase III* activity, and a combinations of all of the aforementioned enzymes or enzyme groups.

The enzyme having DnaA activity is not particularly limited in its biological origin as long as it has an initiator activity that is similar to that of DnaA, which is an initiator protein of *E. coli*, and DnaA derived from *E. coli* may be preferably used. The *Escherichia coli*-derived DnaA may be contained as a monomer in the reaction solution in an amount of 1 nM to 10 µM, preferably in an amount of 1 nM to 5 µM, 1 nM to 3 µM, 1 nM to 1.5 µM, 1 nM to 1.0 µM, 1 nM to 500 nM, 50 nM to 200 nM, or 50 nM to 150 nM, but without being limited thereby.

A nucleoid protein is protein in the nucleoid. The one or more types of nucleoid protein used in the present invention is not particularly limited in its biological origin as long as it has an activity that is similar to that of the nucleoid protein of *E. coli*. For example, *Escherichia coli*-derived IHF, namely, a complex of IhfA and/or IhfB (a heterodimer or a homodimer), or *Escherichia coli*-derived HU, namely, a complex of hupA and hupB can be preferably used. The *Escherichia coli*-derived IHF may be contained as a hetero/homo dimer in a reaction solution in a concentration range of 5 nM to 400 nM. Preferably, the *Escherichia coli*-derived IHF may be contained in a reaction solution in a concentration range of 5 nM to 200 nM, 5 nM to 100 nM, 5 nM to 50 nM, 10 nM to 50 nM, 10 nM to 40 nM, or 10 nM to 30 nM, but the concentration range is not limited thereto. The *Escherichia coli*-derived HU may be contained in a reaction solution in a concentration range of 1 nM to 50 nM, and preferably, may be contained therein in a concentration range of 5 nM to 50 nM or 5 nM to 25 nM, but the concentration range is not limited thereto.

An enzyme or enzyme group having DNA gyrase activity is not particularly limited in its biological origin as long as it has an activity that is similar to that of the DNA gyrase of *E. coli*. For example, a complex of *Escherichia coli*-derived GyrA and GyrB can be preferably used. Such a complex of *Escherichia coli*-derived GyrA and GyrB may be contained as a heterotetramer in a reaction solution in a concentration range of 20 nM to 500 nM, and preferably, may be contained therein in a concentration range of 20 nM to 400 nM, 20 nM to 300 nM, 20 nM to 200 nM, 50 nM to 200 nM, or 100 nM to 200 nM, but the concentration range is not limited thereto.

A single-strand binding protein (SSB) is not particularly limited in its biological origin as long as it has an activity that is similar to that of the single-strand binding protein of *E. coli*. For example, *Escherichia coli*-derived SSB can be preferably used. Such *Escherichia coli*-derived SSB may be contained as a homotetramer in a reaction solution in a concentration range of 20 nM to 1000 nM, and preferably, may be contained therein in a concentration range of 20 nM to 500 nM, 20 nM to 300 nM, 20 nM to 200 nM, 50 nM to 500 nM, 50 nM to 400 nM, 50 nM to 300 nM, 50 nM to 200 nM, 50 nM to 150 nM, 100 nM to 500 nM, or 100 nM to 400 nM, but the concentration range is not limited thereto.

An enzyme having DnaB-type helicase activity is not particularly limited in its biological origin as long as it has an activity that is similar to that of the DnaB of *E. coli*. For example, *Escherichia coli*-derived DnaB can be preferably used. Such *Escherichia coli*-derived DnaB may be contained as a homohexamer in a reaction solution in a concentration range of 5 nM to 200 nM, and preferably, may be contained therein in a concentration range of 5 nM to 100 nM, 5 nM to 50 nM, or 5 nM to 30 nM, but the concentration range is not limited thereto.

An enzyme having DNA helicase loader activity is not particularly limited in its biological origin as long as it has an activity that is similar to that of the DnaC of *E. coli*. For example, *Escherichia coli*-derived DnaC can be preferably used. Such *Escherichia coli*-derived DnaC may be contained as a homohexamer in a reaction solution in a concentration range of 5 nM to 200 nM, and preferably, may be contained therein in a concentration range of 5 nM to 100 nM, 5 nM to 50 nM, or 5 nM to 30 nM, but the concentration range is not limited thereto.

An enzyme having DNA primase activity is not particularly limited in its biological origin as long as it has an activity that is similar to that of the DnaG of *E. coli*. For example, *Escherichia coli*-derived DnaG can be preferably used. Such *Escherichia coli*-derived DnaG may be contained as a monomer in a reaction solution in a concentration range of 20 nM to 1000 nM, and preferably, may be contained therein in a concentration range of 20 nM to 800 nM, 50 nM to 800 nM, 100 nM to 800 nM, 200 nM to 800 nM, 250 nM to 800 nM, 250 nM to 500 nM, or 300 nM to 500 nM, but the concentration range is not limited thereto.

An enzyme having DNA clamp activity is not particularly limited in its biological origin as long as it has an activity that is similar to that of the DnaN of *E. coli*. For example, *Escherichia coli*-derived DnaN can be preferably used. Such *Escherichia coli*-derived DnaN may be contained as a homodimer in a reaction solution in a concentration range of 10 nM to 1000 nM, and preferably, may be contained therein in a concentration range of 10 nM to 800 nM, 10 nM to 500 nM, 20 nM to 500 nM, 20 nM to 200 nM, 30 nM to 200 nM, or 30 nM to 100 nM, but the concentration range is not limited thereto.

An enzyme or enzyme group having DNA polymerase III* activity is not particularly limited in its biological origin as long as it is an enzyme or enzyme group having an activity that is similar to that of the DNA polymerase III* complex of *E. coli*. For example, an enzyme group comprising any of *Escherichia coli*-derived DnaX, HolA, HolB, HolC, HolD, DnaE, DnaQ, and HolE, preferably, an enzyme group comprising a complex of *Escherichia coli*-derived DnaX, HolA, HolB, and DnaE, and more preferably, an enzyme comprising a complex of *Escherichia coli*-derived DnaX, HolA, HolB, HolC, HolD, DnaE, DnaQ, and HolE, can be preferably used. Such an *Escherichia coli*-derived DNA polymerase III* complex may be contained as a heteromultimer in a reaction solution in a concentration range of 2 nM to 50 nM, and preferably, may be contained therein in a concentration range of 2 nM to 40 nM, 2 nM to 30 nM, 2 nM to 20 nM, 5 nM to 40 nM, 5 nM to 30 nM, or 5 nM to 20 nM, but the concentration range is not limited thereto.

2. Second Enzyme Group

In the present description, the second enzyme group means an enzyme group that that catalyzes an Okazaki fragment maturation and synthesizes two sister circular DNAs constituting a catenane.

In the present invention, the two sister circular DNAs constituting a catenane are two circular DNAs synthesized by DNA replication, then joined together.

Examples of second enzyme groups that catalyze an Okazaki fragment maturation and synthesize two sister circular DNAs constituting a catenane may include, for example, one or more enzymes selected from the group consisting of an enzyme having DNA polymerase I activity, an enzyme having DNA ligase activity, and an enzyme having RNaseH activity, or a combination of these enzymes.

An enzyme having DNA polymerase I activity is not particularly limited in its biological origin as long as it has an activity that is similar to DNA polymerase I of *E. coli*. For example, *Escherichia coli*-derived DNA polymerase I can be preferably used. Such *Escherichia coli*-derived DNA polymerase I may be contained as a monomer in a reaction solution in a concentration range of 10 nM to 200 nM, and preferably, may be contained therein in a concentration range of 20 nM to 200 nM, 20 nM to 150 nM, 20 nM to 100 nM, 40 nM to 150 nM, 40 nM to 100 nM, or 40 nM to 80 nM, but the concentration range is not limited thereto.

An enzyme having DNA ligase activity is not particularly limited in its biological origin as long as it has an activity that is similar to DNA ligase of *E. coli*. For example, *Escherichia coli*-derived DNA ligase or the DNA ligase of T4 phage can be preferably used. Such *Escherichia coli*-derived DNA ligase may be contained as a monomer in a reaction solution in a concentration range of 10 nM to 200 nM, and preferably, may be contained therein in a concentration range of 15 nM to 200 nM, 20 nM to 200 nM, 20 nM to 150 nM, 20 nM to 100 nM, or 20 nM to 80 nM, but the concentration range is not limited thereto.

The enzyme having RNaseH activity is not particularly limited in terms of biological origin, as long as it has the activity of decomposing the RNA chain of an RNA-DNA hybrid. For example, *Escherichia coli*-derived RNaseH can be preferably used. Such *Escherichia coli*-derived RNaseH may be contained as a monomer in a reaction solution in a concentration range of 0.2 nM to 200 nM, and preferably, may be contained therein in a concentration range of 0.2 nM to 200 nM, 0.2 nM to 100 nM, 0.2 nM to 50 nM, 1 nM to 200 nM, 1 nM to 100 nM, 1 nM to 50 nM, or 10 nM to 50 nM, but the concentration range is not limited thereto.

3. Third Enzyme Group

In the present description, the third enzyme group means an enzyme group that catalyzes a separation of two sister circular DNAs An example of a third enzyme group that catalyzes a separation of two sister circular DNAs is an enzyme group set forth in, for example, the enzyme group described in Peng H & Marians K J. PNAS. 1993, 90: 8571-8575. Specifically, examples of the third enzyme group include one or more enzymes selected from a group consisting of an enzyme having topoisomerase IV activity, an enzyme having topoisomerase III activity, and an enzyme having RecQ-type helicase activity; or a combination of the aforementioned enzymes.

The enzyme having topoisomerase III activity is not particularly limited in terms of biological origin, as long as it has the same activity as that of the topoisomerase III of *Escherichia coli*. For example, *Escherichia coli*-derived topoisomerase III can be preferably used. Such *Escherichia coli*-derived topoisomerase III may be contained as a monomer in a reaction solution in a concentration range of 20 nM to 500 nM, and preferably, may be contained therein in a concentration range of 20 nM to 400 nM, 20 nM to 300 nM, 20 nM to 200 nM, 20 nM to 100 nM, or 30 nM to 80 nM, but the concentration range is not limited thereto.

The enzyme having RecQ-type helicase activity is not particularly limited in terms of biological origin, as long as it has the same activity as that of the RecQ of *Escherichia coli*. For example, *Escherichia coli*-derived RecQ can be preferably used. Such *Escherichia coli*-derived RecQ may be contained as a monomer in a reaction solution in a concentration range of 20 nM to 500 nM, and preferably, may be contained therein in a concentration range of 20 nM to 400 nM, 20 nM to 300 nM, 20 nM to 200 nM, 20 nM to 100 nM, or 30 to 80 nM, but the concentration range is not limited thereto.

An enzyme having topoisomerase IV activity is not particularly limited in its biological origin as long as it has an activity that is similar to topoisomerase IV of *E. coli*. For example, *Escherichia coli*-derived topoisomerase IV that is a complex of ParC and ParE can be preferably used. Such *Escherichia coli*-derived topoisomerase IV may be contained as a heterotetramer in a reaction solution in a concentration range of 0.1 nM to 50 nMM, and preferably, may be contained therein in a concentration range of 0.1 nM to 40 nM, 0.1 nM to 30 nM, 0.1 nM to 20 nM, 1 nM to 40 nM, 1 nM to 30 nM, 1 nM to 20 nM, 1 nM to 10 nM, or 1 nM to 5 nM, but the concentration range is not limited thereto.

The first, second and third enzyme groups given above may be those that are commercially available, or they may be extracted from microorganisms and purified as necessary. Extraction and purification of enzymes from microorganisms may be performed as necessary using means that are available to a person skilled in the art.

When enzymes other than the above described *Escherichia coli*-derived enzymes are used as the first, second and third enzyme groups, they may be each used in a concentration range corresponding, as an enzyme activity unit, to the concentration range that is specified with respect to the above described *Escherichia coli*-derived enzyme.

The reaction solution containing cell-free protein expression systems of the above mentioned enzymes may be mixed as-is with the circular DNA that constitutes a template to form a reaction mixture for replicating or amplifying circular DNA. The cell-free protein expression system may be a cell-free translation system that comprises a total RNA containing RNA consisting of a sequence that is complementary to the base sequence of genes encoding the above enzymes, mRNA or in vitro transcription product as the template RNA, or it may be a cell-free transcription/translation system that comprises genes encoding different enzymes or expression vectors including genes that encode different enzymes as the template DNA.

<Method for Replicating Circular DNA (A)

In one aspect, the present application relates to a method for replicating or amplifying circular DNA in a cell-free system, comprising the following steps:

(1) forming a reaction mixture of circular DNA as a template with a reaction solution comprising:

a first enzyme group that catalyzes replication of circular DNA, a second enzyme group that catalyzes an Okazaki fragment maturation and synthesizes two sister circular DNAs constituting a catenane, and a third enzyme group that catalyzes a separation of two sister circular DNAs; and (2) reacting the reaction mixture formed in step (1), wherein the circular DNA includes a replication origin sequence (origin of chromosome (oriC)) that can bind to an enzyme having DnaA activity, and further includes a pair of ter sequences that are each inserted outward with respect to oriC, and/or a nucleotide sequence recognized by XerCD, wherein when the circular DNA has the ter sequences, the reaction solution in step (1) further comprises a protein having an activity of inhibiting replication by binding to the ter sequences, and when the circular DNA has the nucleotide sequence recognized by XerCD, the reaction solution in step (1) further comprises a XerCD protein (hereinafter also referred to as "Method (A)" in the present description).

Without being limited by theory, in Method (A), circular DNA is replicated or amplified through the replication cycle shown in FIG. 1 or by repeating this replication cycle. In the present description, replication of circular DNA means that the same molecule as the circular DNA used as a template is generated. Replication of circular DNA can be confirmed by the phenomenon that the amount of circular DNA in the reaction product after completion of the reaction is increased, in comparison to the amount of circular DNA used as a template at initiation of the reaction. Preferably, replication of circular DNA means that the amount of circular DNA in the reaction product is increased at least 2 times, 3 times, 5 times, 7 times, or 9 times, in comparison to the amount of circular DNA at initiation of the reaction. Amplification of circular DNA means that replication of circular DNA progresses and the amount of circular DNA in the reaction product is exponentially increased with respect to the amount of circular DNA used as a template at initiation of the reaction. Accordingly, amplification of circular DNA is one embodiment of replication of circular DNA. In the present description, amplification of circular DNA means that the amount of circular DNA in the reaction product is increased at least 10 times, 50 times, 100 times, 200 times, 500 times, 1000 times, 2000 times, 3000 times, 4000 times, 5000 times, or 10000 times, in comparison to the amount of the amount of circular DNA used as a template at initiation of the reaction.

In the method of the present application, the phrase "in a cell-free system" means that the replication reaction is not performed in cells. That is to say, the method of the present application performed in a cell-free system is intended to mean that the present method is carried out in vitro. The same applies to "Method (B)" described later.

Circular DNA to be mixed with the reaction solution is as described in the above section <circular DNA>. The amount of template DNA used per reaction is not particularly limited. For example, at the initiation of the reaction, the circular DNA may be present in a concentration of 10 ng/µl or less, 5 ng/µl or less, 1 ng/µl or less, 0.8 ng/µl or less, 0.5 ng/µl or less, 0.1 ng/µl or less, 50 pg/µl or less, 5 pg/µl or less, 0.5 pg/µl or less, 50 fg/µl or less, 5 fg/µl or less, or 0.5 fg/µl or less, in the reaction solution. Moreover, at the initiation of the reaction, one molecule of circular DNA per reaction is allowed to be present as a template, so that it can be used in replication or amplification.

The circular DNA used as a template in Method (A) comprises a pair of ter sequences that are each inserted outward with respect to oriC, and/or a nucleotide sequence recognized by XerCD. When this circular DNA has the ter sequences, the reaction solution in step (1) further comprises a protein having an activity of inhibiting replication by binding to the ter sequences, and when the circular DNA has the nucleotide sequence recognized by XerCD, the reaction solution in step (1) further comprises a XerCD protein.

As such a protein having an activity of inhibiting replication by binding to the ter sequences and/or XerCD, a commercially available product may be used, or a product extracted from microorganisms and the like, which is then purified as necessary, may also be used. Extraction and purification of an enzyme from microorganisms may be carried out, as appropriate, by using means available to a person skilled in the art.

A combination of ter sequences on the DNA and a protein having an activity of inhibiting replication by binding to the ter sequences is a mechanism of terminating replication. This mechanism was found in a plurality types of bacteria, and for example, in *Escherichia coli*, this mechanism has been known as a Tus-ter system (Hiasa, H., and Marians, K. J., J. Biol. Chem., 1994, 269: 26959-26968; Neylon, C., et al., Microbiol. Mol. Biol. Rev., September 2005, p. 501-526) and in *Bacillus* bacteria, this mechanism has been known as an RTP-ter system (Vivian, et al., J. Mol. Biol., 2007, 370: 481-491). In the method of the present application, by utilizing this mechanism, generation of a DNA multimer as a by-product can be suppressed. The combination of the ter sequences on the DNA and the protein having an activity of inhibiting replication by binding to the ter sequences is not particularly limited, in terms of the biological origin thereof.

In a preferred embodiment, in the method of the present application, a combination of ter sequences and a Tus protein is used. The ter sequence used in combination with the Tus protein may be a sequence comprising 5'-GN[A/G][T/A]GTTGTAAC[T/G]A-3' (SEQ ID NO: 1), or more preferably, 5'-G[T/G]A[T/A]GTTGTAAC[T/G]A-3' (SEQ ID NO: 2), 5'-GTATGTTGTAACTA-3' (SEQ ID NO: 3), 5'-AGTATGTTGTAACTAAAG-3' (SEQ ID NO: 4), 5'-GGATGTTGTAACTA-3' (SEQ ID NO: 5), 5'-GTATGTTGTAACGA-3' (SEQ ID NO: 6), 5'-GGATGTTGTAACTA-3' (SEQ ID NO: 7), 5'-GGAAGTTGTAACGA-3' (SEQ ID NO: 8), or 5'-GTAAGTTGTAACGA-3' (SEQ ID NO: 9). The origin of the Tus protein is not particularly limited, but it is preferably a Tus protein derived from *Escherichia coli*. The Tus protein may be comprised in a reaction solution in a concentration range of 1 nM to 200 nM, and may be preferably comprised in a concentration range of 2 nM to 200 nM, 2 nM to 100 nM, 5 nM to 200 nM, 5 nM to 100 nM, 10 nM to 100 nM, 20 nM to 100 nM, or 20 nM to 80 nM, but the concentration range is not limited thereto.

Figure 5:
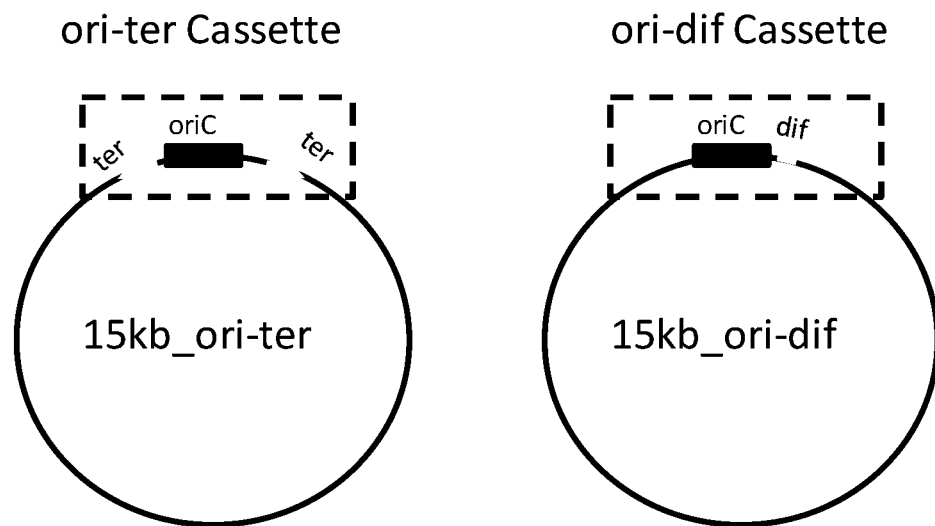
FIG. 5 is a schematic view showing 15 kb ori-ter circular DNA and 15 kb ori-dif circular DNA.

In another preferred embodiment, in the method of the present application, a combination of ter sequences and an RTP protein is used. The ter sequence used in combination with the RTP protein is a sequence with a length of 23 to 30 nucleotides, comprising 5'-AC[T/A][A/G]ANNNNN[C/T]NATGTACNAAAT-3' (SEQ ID NO: 10), or preferably 5'-ACTAATT[A/G]A[A/T]C[T/C]ATGTACTAAAT-3' (SEQ ID NO: 11), 5'-ACTAATT[A/G]A[A/T]C[T/C]ATGTACTAAATTTTCA-3' (SEQ ID NO: 12), 5'-GAACTAATTAAACTATGTACTAAATTTTCA-3' (SEQ ID NO: 13), or 5'-ATACTAATTGATCCATGTACTAAATTTTCA-3' (SEQ ID NO: 14). When a sequence with a length of 23 to 30 nucleotides, comprising any one of sequences shown in SEQ ID NOS: 10 to 12, is selected as a ter sequence, this sequence may have sequence identity of at least 70%, at least 80%, at least 90%, or at least 95% to SEQ ID NO: 13 or 14. The origin of the RTP protein is not particularly limited, but it is preferably an RTP protein derived from *Bacillus* bacteria, and more preferably, an RTP protein derived from *Bacillus subtilis*. The Tus protein may be comprised in a reaction solution in a concentration range of 1 nM to 200 nM, and may be preferably comprised in a concentration range of 2 nM to 200 nM, 2 nM to 100 nM, 5 nM to 200 nM, 5 nM to 100 nM, 10 nM to 100 nM, 20 nM to 100 nM, or 20 nM to 80 nM, but the concentration range is not limited thereto. Regarding the ter sequences, the phrase "inserted outward with respect to oriC" means that the ter sequences are inserted, such that replication performed in the direction of heading outside of oriC is allowed by the action of a combination with a protein having an activity of inhibiting replication by binding to the ter sequences, whereas replication performed in the direction of heading toward oriC is not allowed and is terminated. The arrows of the ter sequences shown in FIG. 3(a) and FIG. 5 show a state in which a pair of ter sequences are each inserted outward with respect to oriC. Accordingly, regarding the ter sequence, the phrase "a pair of ter sequences are each inserted outward with respect to oriC" means that a sequence comprising any one of sequences shown in SEQ ID NOS: 1 to 14 is inserted as one ter sequence into the 5'-terminal side of oriC, and a sequence comprising a complementary sequence to any one of sequences shown in SEQ ID NOS: 1 to 14 is inserted as the other ter sequence into the 3'-terminal side of oriC.

The ter sequences may be present in any positions, as long as a pair of the ter sequences is each inserted outward with respect to oriC. For example, a pair of the ter sequences may be present in a region opposite to oriC, or may also be present in a region close to or adjacent to both sides of oriC. When a pair of the ter sequences is present in a region close to or adjacent to both sides of oriC, the oriC and a pair of the ter sequences can be prepared as a functional cassette. Thus, it is advantageous in that introduction of oriC and a pair of the ter sequences into DNA can be facilitated and the cost of preparing the circular DNA used as a template can be reduced.

A combination of a sequence recognized by XerCD on the DNA and a XerCD protein is a mechanism of separating a DNA multimer (Ip, S. C. Y., et al., EMBO J., 2003, 22: 6399-6407). The XerCD protein is a complex of XerC and XerD. As such a sequence recognized by XerCD, a dif sequence, a cer sequence, and a psi sequence have been known (Colloms, et al., EMBO J., 1996, 15(5): 1172-1181; Arciszewska, L. K., et al., J. Mol. Biol., 2000, 299: 391-403). In the method of the present application, by utilizing this mechanism, generation of a DNA multimer as a by-product can be suppressed. The combination of the sequence recognized by XerCD on the DNA and the XerCD protein is not particularly limited, in terms of the biological origin thereof. Moreover, the promoting factors of XerCD have been known, and for example, the function of dif is promoted by a FtsK protein (Ip, S. C. Y., et al., EMBO J., 2003, 22: 6399-6407). In one embodiment, such a FtsK protein may be comprised in a reaction solution used in the method of the present application.

The sequence recognized by XerCD may be a sequence comprising 5'-GGTGCG[C/T][A/G][T/C]AANNNNNNT-TATG[T/G]TAAA[T/C]-3' (SEQ ID NO: 15), 5'-GGTGCG [C/T]A[T/C]AANNNNNNTTATG[T/G]TAAAT-3' (SEQ ID NO: 16), 5'-GGTGCGC[A/G][T/C]AANNNNNNT-TATGTTAAA[T/C]-3' (SEQ ID NO: 17), 5'-GGTGCG[C/T][A/G]CAANNNNNNTTATG[T/G]TAAA[T/C]-3' (SEQ ID NO: 18), 5'-GGTGCGCATAANNNNNNTTATGT-TAAAT-3' (SEQ ID NO: 19), 5'-GGTGCGTA-CAANNNNNNTTATGGTAAAT-3' (SEQ ID NO: 20), 5'-GGTGCGCGCAANNNNNNTTATGTTAAAC-3' (SEQ ID NO: 21), 5'-GGTGCGCATAATGTATATTATGT-TAAAT-3' (SEQ ID NO: 22/dif sequence), 5'-GGTGCGTA-CAAGGGATGTTATGGTAAAT-3' (SEQ ID NO: 23/cer sequence), or 5'-GGTGCGCGCAAGATCCATTATGT-TAAAC-3' (SEQ ID NO: 24/psi sequence), or a complementary sequence to any one of these sequences. The nucleotide portion at positions 1 to 11 in SEQ ID NOS: 15 to 24 is a XerC binding site, and the nucleotide portion at positions 18 to 28 in SEQ ID NOS: 15 to 24 is a XerD binding site. Since the nucleotide portion at positions 12 to 17 in SEQ ID NOS: 15 to 21 (i.e., a 6-nucleotide portion consisting of NNNNNN) is not a binding region to XerC or XerD, the sequence thereof is not particularly limited.

Preferably, the sequence of the nucleotides at positions 12 to 17 in SEQ ID NOS: 15 to 21 (i.e., a 6-nucleotide portion consisting of NNNNNN) may have sequence identity of at least 70%, at least 80%, at least 90%, or at least 95% to the sequence of the nucleotides at positions 12 to 17 in SEQ ID NOS: 22 to 24.

The XerCD protein is preferably a XerCD protein derived from *Escherichia coli*. The XerCD protein may be comprised in a reaction solution in a concentration range of 1 nM to 200 nM, and may be preferably comprised in a concentration range of 5 nM to 200 nM, 5 nM to 150 nM, 10 nM to 200 nM, 10 nM to 150 nM, 20 nM to 200 nM, 20 nM to 150 nM, or 20 nM to 100 nM, but the concentration range is not limited thereto.

The sequence recognized by XerCD may be present in any position on circular DNA. For example, the sequence recognized by XerCD may be present in a region opposite to oriC, or may also be present in a region close to or adjacent to oriC. When the sequence recognized by XerCD is present in a region close to or adjacent to oriC, the oriC and the sequence recognized by XerCD can be prepared as a functional cassette. Thus, it is advantageous in that introduction of oriC and the sequence recognized by XerCD into DNA can be facilitated and the cost of preparing the circular DNA used as a template can be reduced.

In the present description, the identity (%) between two nucleotide sequences can be determined by visual inspection and mathematical calculation. In addition, the identity (%) can also be determined by using computer programs. Examples of such sequence comparison computer programs may include BLASTN Program, which is available from the website of United States National Library of Medicine (http://www.ncbi.nlm.nih.gov/blast/bl2seq/bls.html) (Altschul et al. (1990) J. Mol. Biol. 215: 403-10); version 2.2.7 or WU-BLAST2.0 Algorithm. With regard to the standard default parameters of WU-BLAST2.0, the default parameters described in the following internet site (http://blast.wustl.edu) may be available.

The first, second and third enzyme groups contained in the reaction solution are as described in the above section <First, second and third enzyme groups>.

In a certain embodiment, the first enzyme group used in the method of the present application may include a combination of, an enzyme having DnaA activity, one or more nucleoid proteins, an enzyme or an enzyme group having DNA gyrase activity, a single-strand DNA binding protein (SSB), an enzyme having DnaB-type helicase activity, an enzyme having DNA helicase loader activity, an enzyme having DNA primase activity, an enzyme having DNA clamp activity, and an enzyme or an enzyme group having DNA polymerase III* activity. Herein, the one or more nucleoid proteins may be IHF or HU, the enzyme or the enzyme group having DNA gyrase activity may be a complex of GyrA and GyrB, the enzyme having DnaB-type helicase activity may be DnaB helicase, the enzyme having DNA helicase loader activity may be a DnaC helicase loader, the enzyme having DNA primase activity may be DnaG primase, the enzyme having DNA clamp activity may be a DnaN clamp, and the enzyme or the enzyme group having DNA polymerase III* activity may be an enzyme or an enzyme group comprising any of DnaX, HolA, HolB, HolC, HolD, DnaE, DnaQ, and HolE.

In another embodiment, the second enzyme group used in the method of the present invention may include a combination of an enzyme having DNA polymerase I activity and an enzyme having DNA ligase activity. Otherwise, the second enzyme group may include a combination of an enzyme having DNA polymerase I activity, an enzyme having DNA ligase activity, and an enzyme having RNaseH activity.

In a further embodiment, the third enzyme group used in the method of the present application may include an enzyme having topoisomerase III activity and/or an enzyme having topoisomerase IV activity. Otherwise, the third enzyme group may include a combination of an enzyme having topoisomerase III activity and an enzyme having RecQ-type helicase activity. Otherwise, the third enzyme group may also be a combination of an enzyme having topoisomerase III activity, an enzyme having RecQ-type helicase activity, and an enzyme having topoisomerase IV activity.

The reaction solution may comprise a buffer, ATP, GTP, CTP, UTP, dNTP, a magnesium ion source, and an alkaline metal ion source.

The buffer contained in the reaction solution is not particularly limited, as long as it is suitably used in a pH range of pH 7 to 9, and preferably at pH 8. Examples of the buffer may include Tris-HCl, Hepes-KOH, a phosphate buffer, MOPS-NaOH, and Tricine-HCl. A preferred buffer is Tris-HCl. The concentration of the buffer can be selected, as appropriate, by a person skilled in the art, and thus, it is not particularly limited. In the case of Tris-HCl, for example, a concentration of 10 mM to 100 mM, 10 mM to 50 mM, or 20 mM can be selected.

ATP means adenosine triphosphate. At the initiation of the reaction, the concentration of ATP contained in the reaction solution may be in a range of, for example, 0.1 mM to 3 mM, and preferably in a concentration range of 0.1 mM to 2 mM, 0.1 mM to 1.5 mM, or 0.5 mM to 1.5 mM.

GTP, CTP and UTP mean guanosine triphosphate, cytidine triphosphate and uridine triphosphate, respectively. At the initiation of the reaction, the concentrations of GTP, CTP and UTP contained in the reaction solution may independently be, for example, in a range of 0.1 mM to 3.0 mM, and preferably in a concentration range of 0.5 mM to 3.0 mM or 0.5 mM to 2.0 mM.

dNTP is a general term for deoxyadenosine triphosphate (dATP), deoxyguanosine triphosphate (dGTP), deoxycytidine triphosphate (dCTP), and deoxythymidine triphosphate (dTTP). At the initiation of the reaction, the concentration of dNTP contained in the reaction solution may be, for example, in a range of 0.01 to 1 mM, and preferably in a concentration range of 0.05 mM to 1 mM or 0.1 mM to 1 mM.

The magnesium ion source is a substance that gives magnesium ions ($Mg^{2+}$) into the reaction solution. Examples of the magnesium ion source may include $Mg(OAc)_2$, $MgCl_2$, and $MgSO_4$. A preferred magnesium ion source is $Mg(OAc)_2$. At the initiation of the reaction, the concentration of the magnesium ion source contained in the reaction solution may be, for example, a concentration that is necessary for giving 5 to 50 mM magnesium ions into the reaction solution.

The alkali metal ion source is a substance that gives alkali metal ions into the reaction solution. Examples of the alkali metal ion may include sodium ions ($Na^+$) and potassium ions ($K^+$). Examples of the alkali metal ion source may include potassium glutamate, potassium aspartate, potassium chloride, potassium acetate, sodium glutamate, sodium aspartate, sodium chloride, and sodium acetate. A preferred alkali metal ion source is potassium glutamate. At the initiation of the reaction, the concentration of the alkali metal ion source contained in the reaction solution may be a concentration that is necessary for giving alkali metal ions in a range of 100 mM to 300 mM, into the reaction solution, but the concentration is not limited thereto. Keeping a good balance with earlier applications, 150 mM may be subtracted from the concentration of the above described alkali metal ion source.

The reaction solution may further comprise a protein non-specific adsorption inhibitor or a nucleic acid non-specific adsorption inhibitor. Preferably, the reaction solution may further comprise a protein non-specific adsorption inhibitor and a nucleic acid non-specific adsorption inhibitor. Because of the presence of such a protein non-specific adsorption inhibitor and/or a nucleic acid non-specific adsorption inhibitor in the reaction solution, non-specific adsorption between proteins and/or between a protein and circular DNA, or adhesion of a protein and circular DNA onto the surface of a vessel can be suppressed, so that the improvement of the reaction efficiency can be expected.

The protein non-specific adsorption inhibitor is a protein that is irrelevant to the replication or amplification reaction in the method of the present application. Examples of such a protein may include bovine serum albumin (BSA), lysozyme, gelatin, heparin, and casein. The protein non-specific adsorption inhibitor may be contained in the reaction solution in a concentration range of 0.02 to 2.0 mg/ml, and preferably in a concentration range of 0.1 to 2.0 mg/ml, 0.2 to 2.0 mg/ml, or 0.5 to 2.0 mg/ml, but the concentration range is not limited thereto.

The nucleic acid non-specific adsorption inhibitor is a nucleic acid molecule or a nucleic acid-like factor that is irrelevant to the replication or amplification reaction in the method of the present application. Examples of such a nucleic acid molecule or a nucleic acid-like factor may include tRNA (transfer RNA), rRNA (ribosomal RNA), mRNA (messenger RNA), glycogen, heparin, oligo DNA, poly(I-C) (polyinosine-polycytidine), poly(dI-dC) (polydeoxyinosine-polydeoxycytidine), poly(A) (polyadenine), and poly(dA) (polydeoxyadenine). The nucleic acid non-specific adsorption inhibitor may be contained in the reaction solution in a concentration range of 1 to 500 ng/µl, and preferably in a concentration range of 10 to 500 ng/µl, 10 to 200 ng/µl, or 10 to 100 ng/µl, but the concentration range is not limited thereto. Keeping a good balance with earlier applications, when tRNA is selected as such a nucleic acid non-specific adsorption inhibitor, 50 ng/µl may be subtracted from the concentration of tRNA.

The reaction solution may further comprise linear DNA-specific exonuclease or RecG-type helicase. Preferably, the reaction solution may further comprise linear DNA-specific exonuclease and RecG-type helicase. Because of the presence of the linear DNA-specific exonuclease and/or the RecG-type helicase in the reaction solution, reducing the amount of linear DNA generated as a result of duplex cleavage or the like during the replication or amplification reaction, and improving the yield of a supercoiled product of interest can be expected.

The linear DNA-specific exonuclease is an enzyme that successively hydrolyzes linear DNA from the 5'-terminus or 3'-terminus thereof. The linear DNA-specific exonuclease is not particularly limited in terms of type or biological origin, as long as it has the activity of successively hydrolyzing linear DNA from the 5'-terminus or 3'-terminus thereof. For example, RecBCD, λ exonuclease, exonuclease III, exonuclease VIII, T5 exonuclease, T7 exonuclease, and Plasmid-Safe™ ATP-Dependent DNase (epicentre) can be used. A preferred linear DNA-specific exonuclease is RecBCD. The linear DNA exonuclease may be contained in the reaction solution in a concentration range of 0.01 to 1.0 U/µL, and preferably in a concentration range of 0.1 to 1.0 U/μL, but the concentration range is not limited thereto. The enzyme activity unit (U) of the linear DNA exonuclease is a unit obtained when the amount of enzyme necessary for converting 1 nmol deoxyribonucleotide of linear DNA to be acid-soluble during a reaction at 37° C. for 30 minutes is set at 1 U.

The RecG-type helicase is an enzyme that is considered to be helicase overcoming a DNA structure generated as a by-product by collision between replication folks at the termination of the elongation reaction. The RecG-type helicase is not particularly limited in terms of biological origin, as long as it has the same activity as that of *Escherichia coli*-derived RecG. For example, the *Escherichia coli*-derived RecG can be preferably used. The *Escherichia coli*-derived RecG may be contained as a monomer in the reaction solution in a concentration range of 100 nM to 800 nM, and preferably in a concentration range of 100 nM to 500 nM, 100 nM to 400 nM, or 100 nM to 300 nM, but the concentration range is not limited thereto. The RecG-type helicase may be used in a concentration range corresponding, as an enzyme activity unit, to the concentration range that is specified with respect to the above described *Escherichia coli*-derived RecG.

The reaction solution may further comprise an ammonium salt. Examples of the ammonium salt may include ammonium sulfate, ammonium chloride, and ammonium acetate. A particularly preferred ammonium salt is ammonium sulfate. The ammonium salt may be contained in the reaction solution in a concentration range of 0.1 mM to 100 mM, and preferably in a concentration range of 0.1 mM to 50 mM, 1 mM to 50 mM, or 1 mM to 20 mM, but the concentration range is not limited thereto.

When the *Escherichia coli*-derived DNA ligase that is an enzyme having DNA ligase activity is used as an enzyme belonging to the second enzyme group, its cofactor, NAD (nicotinamide adenine dinucleotide) is contained in the reaction solution. NAD may be contained in the reaction solution in a concentration range of 0.01 mM to 1.0 mM, and preferably in a concentration range of 0.1 mM to 1.0 mM, or 0.1 mM to 0.5 mM, but the concentration range is not limited thereto.

The reaction solution used in the method of the present invention may further comprise a reducing agent. Examples of a preferred reducing agent may include DTT, β-mercaptoethanol, and glutathione. A preferred reducing agent is DTT.

The reaction solution used in the method of the present invention may further comprise an enzyme and a substrate, which are used for regeneration of ATP. Examples of a combination of an enzyme and a substrate in an ATP regenerating system may include creatine kinase and creatine phosphate, and pyruvate kinase and phosphoenolpyruvate. The enzyme in the ATP regenerating system is, for example, myokinase. A preferred combination of the enzyme and the substrate in the ATP regenerating system is creatine kinase and creatine phosphate.

The above described step (2) is a step pf reacting the reaction mixture formed in step (1). Step (2) may be, for example, a step of reacting the reaction mixture in a temperature range of 15° C. to 80° C., 15° C. to 50° C., or 15° C. to 40° C. Preferably, step (2) may be a step of retaining temperature under an isothermal condition. Such isothermal conditions are not particularly limited, as long as the DNA replication reaction can progress under the conditions. For example, the isothermal conditions may be a constant temperature included in a range of 20° C. to 80° C., or in a range of 25° C. to 50° C., or in a range of 25° C. to 40° C., or at approximately 30° C., which is the optimal temperature of DNA polymerase. In the present description, the terms "retaining under an isothermal condition" and "reacting at an isothermal condition" mean that the temperature is kept in the above described temperature range during the reaction. The time for retaining temperature can be determined, as appropriate, depending on the amount of a replication product or an amplification product of circular DNA of interest. The retaining time can be set to be, for example, 1 to 24 hours.

Alternatively, the method of the present invention may comprise, as the above described step (2), a step of incubating the reaction mixture formed in step (1) in a temperature cycle of repeating incubation at 30° C. or higher and incubation at 27° C. or lower. The incubation at 30° C. or higher is not particularly limited, as long as the temperature is in a temperature range capable of initiating the replication of circular DNA comprising oriC. For example, the temperature may be 30 to 80° C., 30 to 50° C., 30 to 40° C., or 37° C. The incubation at 30° C. or higher may be carried out for 10 seconds to 10 minutes per cycle, although it is not particularly limited thereto. The incubation at 27° C. or lower is not particularly limited, as long as it is a temperature, at which initiation of replication is suppressed and the elongation reaction of DNA progresses. For example, the temperature may be 10 to 27° C., 16 to 25° C., or 24° C. The incubation at 27° C. or lower may be preferably determined depending on the length of circular DNA to be amplified, but is not particularly limited thereto. For example, the incubation may be carried out for 1 to 10 seconds per 1000 bases in a single cycle. The number of temperature cycles is not particularly limited, but may be 10 to 50 cycles, 20 to 40 cycles, 25 to 35 cycles, or 30 cycles.

The method of the present application may include, after completion of the step of incubating the reaction mixture under the isothermal condition, a step of purifying the replication product or amplification product of circular DNA, as required according to the purpose. The purification of circular DNA may be performed as necessary using means available to a person skilled in the art.

The circular DNA that had been replicated or amplified using the method of the present application may be put to use for subsequent purposes, such as transformation, in the form of a reaction mixture after reaction as it is, or in a purified form of the reaction mixture.

<Method for Replicating Circular DNA (A')>

It has been known that, as in the case of the combination of XerCD and dif, even in the case of using a combination of Cre and its recognition sequence loxP, separation of a DNA multimer can be carried out (Ip, S. C. Y., et al., EMBO J., 2003, 22: 6399-6407). The present inventors found that generation of a DNA multimer as a by-product can be suppressed even by using a combination of a DNA multimer separation enzyme and its recognition sequence, instead of the combination of XerCD and dif in Method (A).

In one embodiment, the present application relates to a method for replicating or amplifying circular DNA in a cell-free system, comprising the following steps:

(1) forming a reaction mixture of circular DNA as a template with a reaction solution comprising:
 a first enzyme group that catalyzes replication of circular DNA,
 a second enzyme group that catalyzes an Okazaki fragment maturation and synthesizes two sister circular DNAs constituting a catenane, and a third enzyme group that catalyzes a separation of two sister circular DNAs; and (2) reacting the reaction mixture formed in step (1), wherein the circular DNA includes a replication origin sequence (origin of chromosome (oriC)) that can bind to an enzyme having DnaA activity, and further includes a pair of ter sequences that are each inserted outward with respect to oriC, and/or a nucleotide sequence recognized by a DNA multimer separation enzyme, wherein when the circular DNA has the ter sequences, the reaction solution in step (1) further comprises a protein having an activity of inhibiting replication by binding to the ter sequences, and when the circular DNA has the nucleotide sequence recognized by a DNA multimer separation enzyme, the reaction solution in step (1) further comprises the DNA multimer separation enzyme (hereinafter also referred to as "Method (A')" in the present description).

That is to say, Method (A') is a method in which the "XerCD" in Method (A) is extended to a "DNA multimer separation enzyme," and the "nucleotide sequence recognized by XerCD" in Method (A) is extended to the "nucleotide sequence recognized by the DNA multimer separation enzyme." Accordingly, the explanation made in the <Method for replicating circular DNA (A)> regarding individual configurations of Method (A) is also applied to Method (A').

The DNA multimer separation enzyme is an enzyme that causes genetic recombination so that separation of the DNA multimer can be achieved. A site-specific recombination enzyme, which can recognize a specific nucleotide sequence and can generate genetic recombination at the site of the nucleotide sequence, can be utilized as a DNA multimer separation enzyme. The specific nucleotide sequence recognized by the DNA multimer separation enzyme is referred to as a "nucleotide sequence recognized by a DNA multimer separation enzyme." By carrying out genetic recombination according to a combination of a DNA multimer separation enzyme and a nucleotide sequence recognized by the DNA multimer separation enzyme, a DNA multimer can be separated. In Method (A'), by utilizing this mechanism, generation of a DNA multimer as a by-product can be suppressed. As such a DNA multimer separation enzyme, a commercially available product may be used, or an enzyme extracted from microorganisms and the like, which is then purified as necessary, may also be used. Extraction and purification of an enzyme from microorganisms may be carried out, as appropriate, by using means available to a person skilled in the art.

Examples of the combination of the DNA multimer separation enzyme and the nucleotide sequence recognized by the DNA multimer separation enzyme may include: XerCD and a dif sequence; Cre and a loxP sequence (Siegel, R. W., et al., FEBS Lett., 2001, 499(1-2): 147-153; Araki, K., et al., Nucleic Acids Res.: 1997, 25(4): 868-872); budding yeast (*Saccharomyces verevisiae*)-derived recombinant enzyme FLP and an FRT sequence (Broach, J. R., et al., Cell, 1982, 29(1):227-234); bacteriophage D6-derived recombinant enzyme DreO and a rox sequence (Anastassiadis, K., et al., Dis. Model. Mech., 2009, 2: 508-515); *Zygosacchromyces rouxii*-derived recombinant enzyme R and an RS sequence (Araki, H., et al., J. Mol. Biol., 1985, 182(2): 191-203); and a serine recombinant enzyme family (for example, Gin, γδ, Tn3, and Hin) and the recognition sequences thereof (Smith, M. C., et al., Mol. Microbiol., 2002, 44: 299), but are not limited thereto.

The XerCD and the dif sequence are as described above in the section <Method for replicating circular DNA (A)>.

The combination of Cre and a loxP sequence is not particularly limited, in terms of the biological origin thereof. Cre is preferably a bacteriophage P1-derived Cre protein. Cre may be comprised in a reaction solution in a concentration range of 0.01 to 200 mU/µl, and may be preferably comprised in a concentration range of 0.1 to 150 mU/µl, 0.1 to 100 mU/µl, 0.5 to 100 mU/µl, 0.5 to 80 mU/µl, 0.1 to 50 mU/µl, 1 to 50 mU/µl, or 1 to 30 mU/µl, but the concentration range is not limited thereto.

The loxP sequence recognized by Cre may be a sequence comprising 5'-ATAACTTCGTATAGCATACAT-TATACGAAGTTAT-3' (SEQ ID NO: 30) that is a loxP consensus, or 5'-ATAACTTCGTATAGtATACAT-TATACGAAGTTAT-3' (SEQ ID NO: 31/lox511), 5'-ATAACTTCGTATAGgATACtTTATACGAAGTTAT-3' (SEQ ID NO: 32/lox2272), 5'-ATAACTTCGTATAtaccttc-TATACGAAGTTAT-3' (SEQ ID NO: 33/loxFAS), 5'-ATAACTTCGTATAGCATACATTATACGAAcggta-3' (SEQ ID NO: 34/lox RE), 5'-taccgTTCGTATAGCATACAT-TATACGAAGTTAT-3' (SEQ ID NO: 35/lox LE), that are mutant loxP sequences (wherein the small letter indicates a mutant nucleotide to the consensus), or a complementary sequence to any one of these sequences.

The budding yeast (*Saccharomyces verevisiae*)-derived recombinant enzyme FLP may be comprised in a reaction solution in a concentration range of 1 nM to 200 nM, and may be preferably comprised in a concentration range of 5 nM to 200 nM, 5 nM to 150 nM, 10 nM to 200 nM, 10 nM to 150 nM, 20 nM to 200 nM, 20 nM to 150 nM, or 20 nM to 100 nM, but the concentration range is not limited thereto. The FRT sequence recognized by FLP may be a sequence comprising 5'-GAAGTTCCTATTCTCTAGAAAGTATAG-GAACTTC-3' (SEQ ID NO: 36), or a complementary sequence thereto.

The bacteriophage D6-derived recombinant enzyme DreO may be comprised in a reaction solution in a concentration range of 1 nM to 200 nM, and may be preferably comprised in a concentration range of 5 nM to 200 nM, 5 nM to 150 nM, 10 nM to 200 nM, 10 nM to 150 nM, 20 nM to 200 nM, 20 nM to 150 nM, or 20 nM to 100 nM, but the concentration range is not limited thereto. The rox sequence recognized by DreO may be a sequence comprising 5'-TAACTTTAAATAATGCCAATTATTTAAAGTTA-3' (SEQ ID NO: 37), or a complementary sequence thereto.

The *Zygosacchromyces rouxii*-derived recombinant enzyme R may be comprised in a reaction solution in a concentration range of 1 nM to 200 nM, and may be preferably comprised in a concentration range of 5 nM to 200 nM, 5 nM to 150 nM, 10 nM to 200 nM, 10 nM to 150 nM, 20 nM to 200 nM, 20 nM to 150 nM, or 20 nM to 100 nM, but the concentration range is not limited thereto. The RS sequence recognized by the enzyme R may be a sequence comprising the sequence disclosed in Araki, H. et al. (J. Mol. Biol., 1985, 182(2): 191-203) or a complementary sequence thereto.

The serine recombinant enzyme family (16, Tn3, Gin, and Hin) may be comprised in a reaction solution in a concentration range of 1 nM to 200 nM, and may be preferably comprised in a concentration range of 5 nM to 200 nM, 5 nM to 150 nM, 10 nM to 200 nM, 10 nM to 150 nM, 20 nM to 200 nM, 20 nM to 150 nM, or 20 nM to 100 nM, but the concentration range is not limited thereto. The serine recombinant enzyme family γδ and Tn3, and their recognition sequence res may each be a sequence comprising the sequence disclosed in Grindley N. D. F. et al. (Cell, 1982, 30: 19-27) or a complementary sequence thereto. The serine recombinant enzyme family Gin and its recognition sequence may each be a sequence comprising the sequence disclosed in Kahmann. R. et al. (Cell, 1985, 41: 771-780) or a complementary sequence thereto. The serine recombinant enzyme family Hin and its recognition sequence may each be a sequence comprising the sequence disclosed in Glasgow. A. C. et al. (J. Biol. Chem., 1989, 264: 10072-10082) or a complementary sequence thereto.

The sequence recognized by the DNA multimer separation enzyme may be present in any position on circular DNA. For example, the sequence recognized by the DNA multimer separation enzyme may be present in a region close to or adjacent to oriC, or may also be present in a region opposite to oriC.

<Method for Replicating Circular DNA (B)>

In one embodiment, the present application relates to a method for replicating or amplifying circular DNA in a cell-free system, comprising the following steps:

(1) preparing circular DNA comprising oriC by:
adding an oriC transposon and transposase into a buffer to form an oriC transposome, wherein the oriC transposon is linear DNA comprising a replication origin sequence (origin of chromosome (oriC)) that can bind to an enzyme having DnaA activity, and comprising outside end (OE) sequences at both termini thereof; and
reacting the oriC transposome with circular DNA comprising no oriC in a buffer to carry out a transfer reaction, (2) forming a reaction mixture of the circular DNA comprising oriC obtained in step (1) with a reaction solution comprising:
a first enzyme group that catalyzes replication of circular DNA,
a second enzyme group that catalyzes an Okazaki fragment maturation and synthesizes two sister circular DNAs constituting a catenane, and
a third enzyme group that catalyzes a separation of two sister circular DNAs; and (3) reacting the reaction mixture formed in step (2) (hereinafter also referred to as "Method (B)" in the present description).

Figure 2:
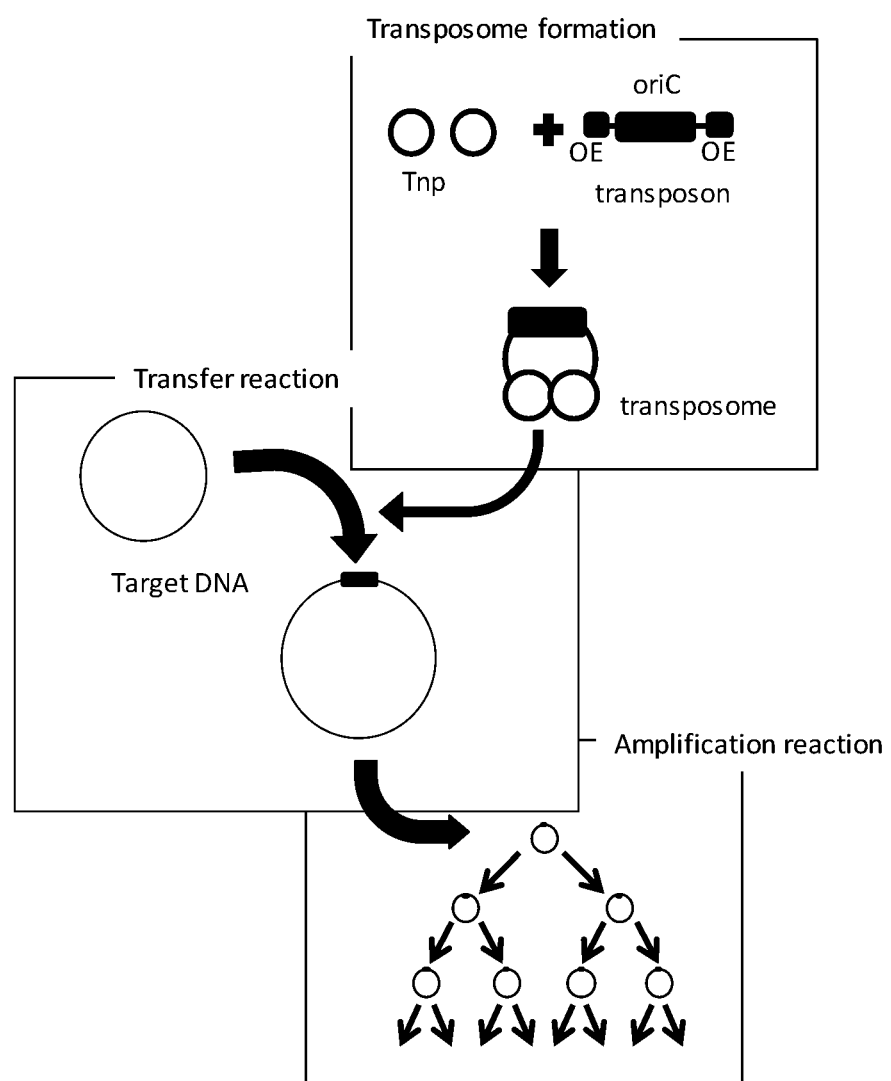
FIG. 2 is an outline view showing oriC cassette introduction by utilizing a transposon and the subsequent replication or amplification reaction.

Without being limited by theory, in Method (B), oriC is introduced into circular DNA comprising no oriC, by using a transposon, so as to prepare circular DNA comprising oriC, and thereafter, the present circular DNA comprising oriC is replicated or amplified. An outline view is shown in FIG. 2. The step indicated with the terms "Transposome formation" and "Transfer reaction" in FIG. 2 corresponds to the above described step (1). With regard to replication or amplification, in the above described steps (2) and (3), circular DNA is replicated or amplified through the replication cycle shown in FIG. 1, or by repeating this replication cycle. The definitions of replication and amplification of circular DNA are as described above.

The circular DNA comprising oriC to be mixed with the reaction solution is as described in the above section <Circular DNA>. The amount of the circular DNA comprising oriC used in a single reaction is as described above regarding the amount of template DNA used in Method (A).

Moreover, the explanation regarding the enzyme groups comprised in the reaction solution and other components optionally comprised in the reaction solution is the same as that for Method (A). Furthermore, the above described step (3) is carried out in the same manner as step (2) in Method (A). The method further comprising a step of purifying the replication product or amplification product of the circular DNA and utilization of the circular DNA replicated or amplified by applying the method of the present application are also the same as those in Method (A).

The OE sequences at both termini of the oriC transposon may be any sequences, as long as it has been known to a person skilled in the art that the sequences are recognized by transposase and can be used as OE sequences. In a preferred embodiment, the OE sequence comprises the sequence shown in SEQ ID NO: 25 (5'-CTGTCTCTTATACACATCT-3') or a complementary sequence thereto, and the OE sequence comprising the sequence shown in SEQ ID NO: 25 is inserted into the 5'-terminus of the linear DNA in step (1), and the OE sequence comprising a complementary sequence to the sequence shown in SEQ ID NO: 25 is inserted into the 3'-terminus of the linear DNA.

In the above described step (1), the concentration of the oriC transposon used in formation of the oriC transposome may be 20 to 200 nM, and may be preferably 40 to 160 nM.

The biological origin of the transposase is not particularly limited, as long as it is an enzyme that recognizes the OE sequence, forms a transposome, and transfers transposon DNA into circular DNA. For example, *Escherichia coli*-derived transposase can be preferably used. A highly active Tn5 mutant (E54K, L372P) protein is particularly preferable (Goryshin, I. Y., and Reznikoff, W. S., J. Biol. Chem., 1998, 273: 7367-7374). As such transposase, a commercially available product may be used, or an enzyme extracted from microorganisms, which is then purified as necessary, may also be used. Extraction and purification of the enzyme from microorganisms may be carried out, as appropriate, by using means available to a person skilled in the art. When a highly active Tn5 mutant (E54K, L372P) protein is used as such transposase, the concentration of the protein used in the formation of the oriC transposome in the above described step (1) may be 50 to 200 nM, and may be preferably 80 to 150 nM.

The buffer used in step (1) is not particularly limited, as long as it is suitable to be used at pH 6 to 9, and preferably at pH 7.5. Examples of the buffer may include Tris-acetic acid, Tris-HCl, Hepes-KOH, a phosphate buffer, MOPS-NaOH, and Tricine-HCl. The preferred buffer is Tris-acetic acid or Tris-HCl. The concentration of the buffer is not particularly limited, and can be selected, as appropriate, by a person skilled in the art. When the buffer is Tris-acetic acid or Tris-HCl, for example, a concentration of 10 mM to 100 mM, 10 mM to 50 mM, or 20 mM may be selected.

In step (1), the step of forming an oriC transposome is carried out by incubation at a temperature of approximately 30° C. for approximately 30 minutes.

The transfer reaction in step (1) is carried out at an optimal temperature of transposase, which is, for example, 37° C. The time required for the transfer reaction can be selected, as appropriate, by a person skilled in the art, and it may be, for example, approximately 15 minutes. Moreover, in the transfer reaction in step (1), tRNA may be added. With regard to the concentration of the tRNA added in the transfer reaction in step (1), for example, a concentration of 10 to 200 ng/μl, 30 to 100 ng/μl, or 50 ng/μl may be selected.

In one embodiment, the circular DNA comprising oriC in step (2) may further comprise a pair of ter sequences that are each inserted outward with respect to oriC, and/or a nucleotide sequence recognized by a DNA multimer separation enzyme such as XerCD or Cre. In this case, when the circular DNA has the ter sequences, the reaction solution in step (2) further comprises a protein having an activity of inhibiting replication by binding to the ter sequences, and when the circular DNA has the nucleotide sequence recognized by a DNA multimer separation enzyme such as XerCD or Cre, the reaction solution in step (2) further comprises the DNA multimer separation enzyme such as XerCD or Cre.

Otherwise, in another embodiment, a pair of ter sequences that are each inserted outward with respect to oriC, and/or a nucleotide sequence recognized by a DNA multimer separation enzyme such as XerCD or Cre are prepared such that they are comprised in a part of the oriC transposon, so that a pair of the ter sequences and/or the nucleotide sequence recognized by the DNA multimer separation enzyme such as XerCD or Cre may also be introduced into circular DNA by utilizing the transposon. Specifically, in this embodiment, the linear DNA in step (1) further comprises a pair of ter sequences that are each inserted outward with respect to oriC, and/or a nucleotide sequence recognized by a DNA multimer separation enzyme such as XerCD or Cre; and when the linear DNA has the ter sequences, the reaction solution in step (2) further comprises a protein having an activity of inhibiting replication by binding to the ter sequences; and when the circular DNA has the nucleotide sequence recognized by a DNA multimer separation enzyme such as XerCD or Cre, the reaction solution in step (2) further comprises a XerCD protein.

Herein, definitions and explanations regarding a pair of the ter sequences that are each inserted outward with respect to oriC, and/or the nucleotide sequence recognized by a DNA multimer separation enzyme such as XerCD or Cre, and the protein having an activity of inhibiting replication by binding to the ter sequences and/or the DNA multimer separation enzyme such as XerCD or Cre are the same as those described above regarding Method (A) or Method (A').

In one embodiment, Method (B) may further comprise a step (4) of removing the oriC transposon from the circular DNA replicated or amplified in the reaction product in step (3).

The step of removing the oriC transposon may comprise a treatment with transposase in a concentration of 0.1 to 30 nM, preferably 1 to 20 nM, and more preferably 3 to 10 nM, and a treatment of converting the terminus of DNA to a single strand by using straight-chain double-stranded DNA dependent single-stranded DNA exonuclease, such as ExoIII. The buffer used in the treatment with transposase may be the buffer used in step (1). The buffer used in the treatment with the single-stranded DNA exonuclease may be a buffer with any composition, as long as the single-stranded DNA exonuclease can act therein.

Moreover, the step of removing the oriC transposon may further comprise a treatment using a restriction enzyme corresponding to a restriction enzyme site comprised in the sequence of the oriC transposon. This treatment is directed towards specifically cleaving the oriC transposon. Therefore, in this case, a restriction enzyme corresponding to a restriction enzyme site, which is comprised in the oriC transposon but is not comprised in a region other than the oriC transposon region in the replicated and/or amplified circular DNA, is selected. For the double strand cleavage that is specific to the region comprised in the oriC transposon, CRISPR-Cas9 may be used instead of the restriction enzyme. In this case, a sequence specific to the region comprised in the oriC transposon is designated as guide RNA.

<Functional Cassette (Nucleic Acid)>

In one aspect, the present application relates to a nucleic acid comprising oriC, and a pair of ter sequences that are each inserted outward with respect to the oriC and/or a nucleotide sequence recognized by a DNA multimer separation enzyme such as XerCD or Cre. The nucleic acid is preferably linear DNA, and is more preferably a double-stranded nucleic acid. The length of the nucleic acid is not particularly limited, as long as the nucleic acid can be utilized in preparation of circular DNA. In a preferred embodiment, the length of the nucleic acid is 273 bp to 2.0 kb, 273 bp to 1.5 kb, or 273 bp to 1.0 kb. The shortest length of the nucleic acid is 273 bp. Since the length of the oriC is 245 bp, and the length of a dif sequence that is the shortest sequence among a pair of the ter sequences and the DNA multimer separation enzyme recognition sequence is 28 bp, the length of 273 bp is a length obtained by directly connecting the two above sequences with each other.

The above described nucleic acid can be utilized as a functional cassette for preparing the circular DNA used as a template in the method (A) of the present application.

In another embodiment, the present application relates to a nucleic acid comprising oriC, and a pair of ter sequences that are each inserted outward with respect to the oriC and/or a nucleotide sequence recognized by a DNA multimer separation enzyme such as XerCD or Cre, and further, outside end (OE) sequences at both termini thereof. The nucleic acid is preferably linear DNA, and is more preferably a double-stranded nucleic acid. The length of the nucleic acid is not particularly limited, as long as the nucleic acid can be utilized in preparation of circular DNA. In a preferred embodiment, the length of the nucleic acid is 311 bp to 2.0 kb, 311 bp to 1.5 kb, or 311 bp to 1.0 kb. The shortest length of the nucleic acid is 311 bp. The length of the oriC is 245 bp, and the length of a dif sequence that is the shortest sequence among a pair of the ter sequences and the DNA multimer separation enzyme recognition sequence is 28 bp, and further, the length of the two OE sequences is 38 bp. Thus, the length of 311 bp is a length obtained by directly connecting these sequences with one another.

The above described nucleic acid can be utilized as a functional cassette that acts as an oriC transposon in the method (B) of the present application.

Herein, definitions and explanations regarding a pair of the ter sequences that are each inserted outward with respect to oriC, and/or the nucleotide sequence recognized by a DNA multimer separation enzyme such as XerCD or Cre, and the protein having an activity of inhibiting replication by binding to the ter sequences and/or the DNA multimer separation enzyme such as XerCD or Cre are the same as those described above regarding Method (A) or Method (A').

The above described functional cassette is advantageous in that the cost of preparing circular DNA comprising oriC, which is used as a template in Methods (A), (A') and (B), can be reduced.

<Kit>

In one aspect, the present application relates to a kit for replicating or amplifying circular DNA, comprising a combination of:

a first enzyme group that catalyzes replication of circular DNA;

a second enzyme group that catalyzes an Okazaki fragment maturation and synthesizes two sister circular DNAs constituting a catenane;

a third enzyme group that catalyzes a separation of two sister circular DNAs;

linear DNA comprising oriC, and a pair of ter sequences that are each inserted outward with respect to the oriC and/or a nucleotide sequence recognized by a DNA multimer separation enzyme such as XerCD or Cre; and when the linear DNA has the ter sequences, a protein having an activity of inhibiting replication by binding to the ter sequences, and/or when the linear DNA has the nucleotide sequence recognized by a DNA multimer separation enzyme such as XerCD or Cre, the DNA multimer separation enzyme corresponding to the sequence, such as XerCD or Cre (hereinafter also referred to as "Kit (A)" in the present description). Kit (A) is a kit for carrying out the method (A) or (A') of the present application.

Specific ingredients and concentrations of individual components included in the Kit (A) of the present invention are the same as those described in the above sections <First, second, and third enzyme groups>, <Method for amplifying circular DNA (A)>, and <Method for amplifying circular DNA (A')>.

In another embodiment, the present application relates to a kit for replicating or amplifying circular DNA, comprising a combination of:

a first enzyme group that catalyzes replication of circular DNA;

a second enzyme group that catalyzes an Okazaki fragment maturation and synthesizes two sister circular DNAs constituting a catenane;

a third enzyme group that catalyzes a separation of two sister circular DNAs;

an oriC transposon, which is linear DNA comprising a replication origin sequence (origin of chromosome (oriC)) that can bind to an enzyme having DnaA activity, and comprising outside end (OE) sequences at both termini thereof; and transposase (hereinafter also referred to as "Kit (B)" in the present description). Kit (B) is a kit for carrying out the method (B) of the present application.

In a certain embodiment, the oriC transposon included in Kit (B) may further comprise a pair of ter sequences that are each inserted outward with respect to oriC, and/or a nucleotide sequence recognized by a DNA multimer separation enzyme such as XerCD or Cre. In this case, Kit (B) may further include a protein having an activity of inhibiting replication by binding to the ter sequences, and/or a DNA multimer separation enzyme corresponding to the sequence recognized by the DNA multimer separation enzyme inserted into the oriC transposon.

The specific component and concentration of each constitutional component included in the kit (B) of the present invention are as described in the above sections <First, second and third enzyme groups>, and <Method for amplifying circular DNA (B)>.

The kits (A) and (B) of the present application may be one kit comprising all of the above described constitutional components. Otherwise, if the kit of the present application is a kit for the purpose of being utilized in the method of the present application, it may not comprise some of the above described constitutional components. When the present kit is a kit that does not comprise some of the above described constitutional components, a practitioner may add necessary components to the kit upon amplification, so as to carry out the amplification methods (A) and (B) of the present application.

The kits (A) and (B) of the present invention may further comprise additional constitutional components comprising one or more components selected from a protein non-specific adsorption inhibitor, a nucleic acid non-specific adsorption inhibitor, linear DNA-specific exonuclease, RecG-type helicase, an ammonium salt, NAD, a reducing agent, and a combination of an enzyme and a substrate in the ATP regenerating system. Such additional constitutional components may be included as a single kit in the kit of the present application, or they may be provided as another kit, which is on premise of being used together with the kit of the present application.

The kits (A) and (B) of the present application may include a mixture of the above described constitutional components, which is packaged as a single item. Otherwise, the kit of the present invention may include the above described constitutional components, which are each packaged separately, or the kit of the present invention may also include several types of constitutional components, which are gathered or mixed, and then packaged. Furthermore, the kits (A) and (B) of the present invention may include an instruction manual including instructions for carrying out the methods (A) and (B) for amplifying circular DNA of the present application.

EXAMPLES

The present invention is explained specifically based on the EXAMPLES. Note that the present invention is not limited to the range set forth in the following Examples.

Example 1: Replication of Circular DNA Associated with Suppression of DNA Multimer by Utilizing Termination Sequence Ter and Tus Protein <Materials and Methods>

Circular DNA to be used as a template was prepared as follows. An oriC fragment was inserted into an M13mp18 plasmid vector to produce 8.0-kb circular DNA. Into a region opposite to oriC in this 8.0-kb circular DNA, a DNA fragment comprising two ter sequences (underlined) facing to each other

was inserted, to produce ter-inserted 8.0-kb circular DNA (FIG. 3(a)). This ter-inserted 8.0-kb circular DNA was used as template DNA, and the aforementioned 8.0-kb circular DNA was used as control DNA that did not comprise a ter sequence.

Tus was prepared by generating it from a Tus-expressing *Escherichia coli* strain according to a step comprising affinity column chromatography and gel filtration column chromatography.

A reaction solution having the composition shown in Table 1, and a reaction solution having the composition shown in Table 1, to which Tus was added to a final concentration of 2 nM or 5 nM, were prepared. To each of these reaction solutions, template DNA or control DNA was added to a final concentration of 0.8 ng/µl, and they were then mixed with each other on ice. Thereafter, the obtained mixture was incubated in an incubator at 30° C. for 1 hour for reaction. The total volume for a single reaction was set at 10 microliter. To the reaction solution, [$\alpha$-$^{32}$P]dATP had been added, and after completion of a DNA replication reaction, an aliquot of the reaction solution was subjected to agarose gel electrophoresis (0.5% 1×TAE, 150 V, 100 minutes, 14° C.). Thereafter, a $^{32}$P incorporated product was detected with BAS Imaging Plate, thereby confirming generation of a supercoiled structure of interest.

TABLE 1

| Reaction buffer | |
| --- | --- |
| Tris-HCl (pH 8.0) | 20 mM |
| Dithiothreitol | 8 mM |
| Potassium glutamate | 150 mM |
| Mg(OAc)$_2$ | 10 mM |
| Creatine phosphate | 4 mM |
| ATP | 1 mM |
| GTP, CTP, UTP | 1 mM each |
| dNTPs | 0.1 mM each |
| tRNA | 50 ng/µL |
| NAD | 0.25 mM |
| Ammonium sulfate | 10 mM |
| Bovine serum albumin (BSA) | 0.5 mg/ml |
| Creatine kinase | 20 ng/µL |
| Enzyme group | |
| SSB | 400 nM |
| IHF | 20 nM |
| DnaG | 400 nM |
| DnaN | 40 nM |
| PolIII* | 5 nM |
| DnaB, DnaC | 20 nM |
| DnaA | 100 nM |
| RNaseH | 10 nM |
| Ligase | 50 nM |
| PolI | 50 nM |
| GyrA, GyrB | 50 nM |
| Topo IV | 5 nM |
| Topo III | 50 nM |
| RecQ | 50 nM |

In the table, SSB indicates SSB derived from *E. coli*, IHF indicates a complex of IhfA and IhfB derived from *E. coli*, DnaG indicates DnaG derived from E. col, DnaN indicates DnaN derived from *E. coli*, PolIII* indicates DNA polymerase III* complex consisting of a complex of DnaX, HolA, HolB, HolC, HolD, DnaE, DnaQ, and HolE, DnaB indicates DnaB derived from *E. coli*, DnaC indicates DnaC derived from *E. coli*, DnaA indicates RNaseH derived from *E. coli*, Ligase indicates DNA ligase derived from *E. coli*, PolI indicates DNA polymerase I derived from *E. coli*, GyrA indicates GyrA derived from *E. coli*, GyrB indicates GyrB derived from *E. coli*, Topo IV indicates a complex of ParC and ParE derived from *E. coli*, Topo III indicates topoisomerase III derived from *E. coli*, and RecQ indicates RecQ derived from *E. coli*.

SSB was prepared by purifying an *E. coli* strain expressing SSB by steps that include ammonium sulfate precipitation and ion-exchange column chromatography.

IHF was prepared by purifying an *E. coli* strain coexpressing IhfA and IhfB by steps that include ammonium sulfate precipitation and affinity column chromatography.

DnaG was prepared by purifying an *E. coli* strain expressing DnaG by steps that include ammonium sulfate precipitation and anion-exchange column chromatography and gel filtration column chromatography.

DnaN was prepared by purifying an *E. coli* strain expressing DnaN by steps that include ammonium sulfate precipitation and anion-exchange column chromatography.

PolIII* was prepared by purifying an *E. coli* strain coexpressing DnaX, HolA, HolB, HolC, HolD, DnaE, DnaQ, and HolE by steps that include ammonium sulfate precipitation, affinity column chromatography and gel filtration column chromatography.

DnaB and DnaC were prepared by purifying an *E. coli* strain coexpressing DnaB and DnaC by steps that include ammonium sulfate precipitation, affinity column chromatography and gel filtration column chromatography.

DnaA was prepared by purifying an *E. coli* strain expressing DnaA by steps that include ammonium sulfate precipitation, dialysis precipitation, and gel filtration column chromatography.

GyrA and GyrB were prepared by purifying a mixture of an *E. coli* strain expressing GyrA and an *E. coli* strain expressing GyrB by steps that include ammonium sulfate precipitation, affinity column chromatography and gel filtration column chromatography.

Topo IV was prepared by purifying a mixture of an *E. coli* strain expressing ParC and an *E. coli* strain expressing ParE by steps that include ammonium sulfate precipitation, affinity column chromatography and gel filtration column chromatography.

Topo III was prepared by purifying an *E. coli* strain expressing Topo III by steps that include ammonium sulfate precipitation, and affinity column chromatography.

RecQ was prepared by purifying an *E. coli* strain expressing RecQ by steps that include ammonium sulfate precipitation, affinity column chromatography and gel filtration column chromatography.

Commercially available enzymes derived from *E. coli* were used for RNaseH, Ligase and PolI (Takara Bio Inc.).

<Results>

Figure 3:
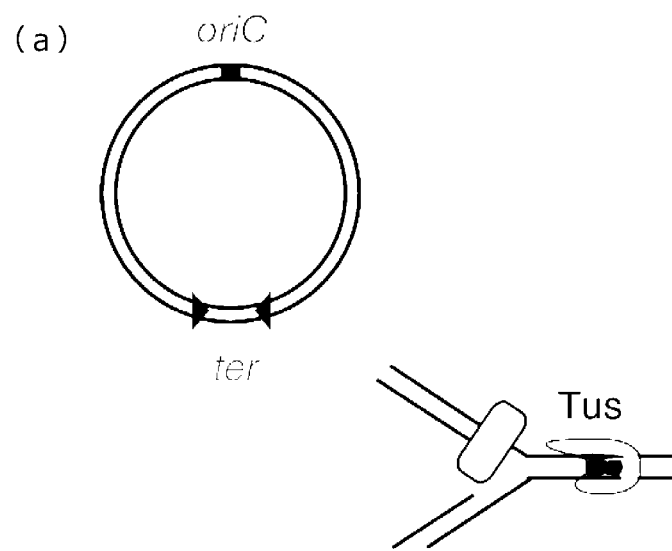
FIG. 3 includes an outline view (a) showing suppression of generation of a DNA multimer by utilizing the termination sequence ter and a Tus protein, and a gel electrophoretic photograph (b) showing the results thereof.
Figure 3:
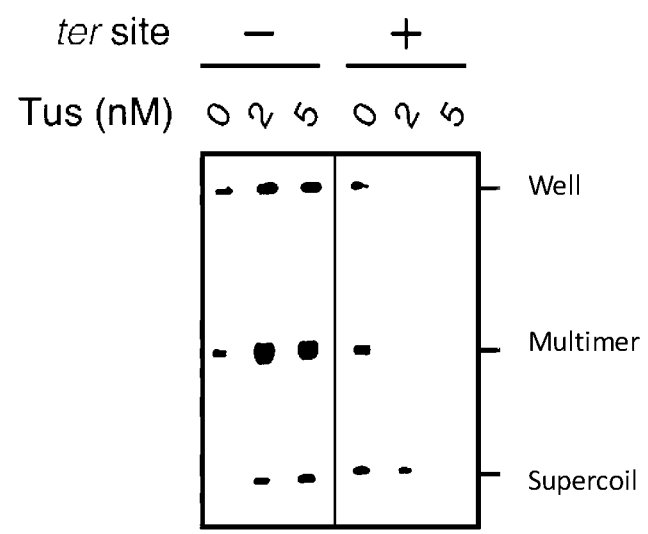

The detection result of a replication product is shown in FIG. 3.

It could be confirmed that, when the ter-inserted 8.0-kb circular DNA was used as a template and Tus was comprised in the reaction solution, circular DNA having a supercoiled structure of interest was replicated or amplified, while suppressing generation of a multimer as a by-product. On the other hand, when the 8.0-kb circular DNA not comprising a ter sequence was used as a template and the reaction solution did not comprise Tus, generation of circular DNA having a supercoiled structure of interest was observed, but at the same time, generation of a multimer as a by-product was also observed.

The Tus-ter system is a mechanism of terminating replication of a circular chromosome. According to the experimental results shown in the present example, it was confirmed that generation of a non-specific DNA multimer can be suppressed by incorporating this system into a reaction of replicating or amplifying circular DNA.

Figure 4:
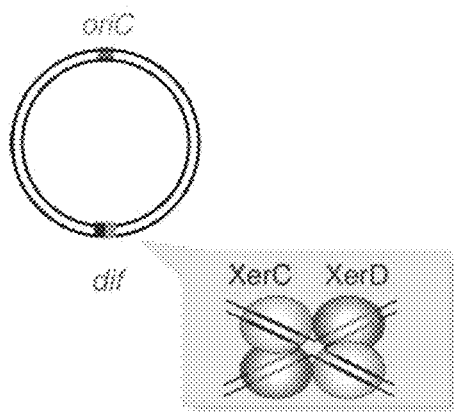
FIG. 4 includes an outline view (a) showing suppression of generation of a DNA multimer by utilizing the site-specific recombination sequences dif and XerCD, and a gel electrophoretic photograph (b) showing the results thereof.
Figure 4:
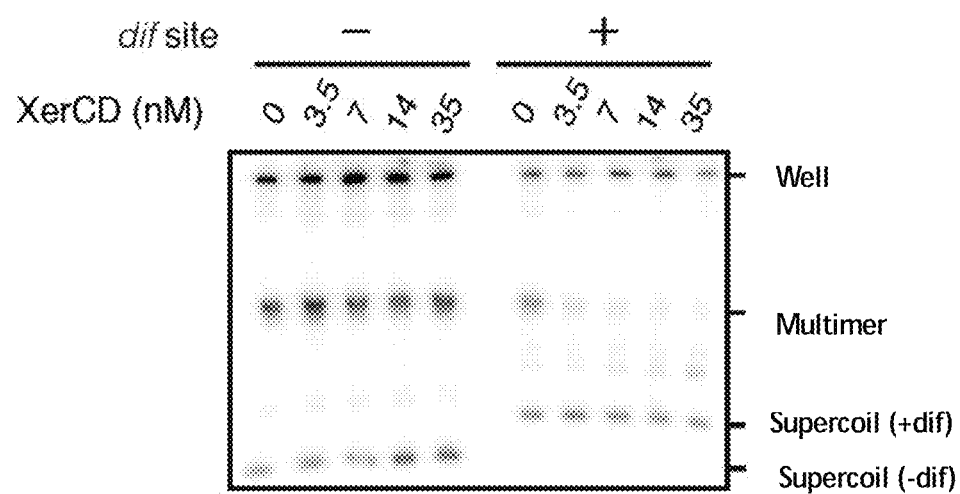

Example 2: Replication of Circular DNA Associated with Suppression of DNA Multimer by Utilizing Site-Specific Recombination Sequences Dif and XerCD <Materials and Methods> dif-inserted 12-kb circular DNA to be used as a template was prepared by performing a recombination reaction in *Escherichia coli* cells so that the dif sequence (SEQ ID NO: 22) was comprised in a region opposite to the oriC of the circular DNA (FIG. 4(*a*)). Specifically, using *Escherichia coli* expressing a recombination protein group of X phage, an intracellular recombination reaction was carried out to prepare circular DNA with a desired length including a cassette comprising oriC and a kanamycin resistance gene, and a 4.2 kb region upstream and a 6.0 kb region downstream of dif in the *Escherichia coli* chromosome.

As control DNA not comprising a dif sequence, the 8.0-kb circular DNA described in Example 1 was used.

XerCD was prepared by purifying it from a XerC and XerD co-expressing *Escherichia coli* strain according to a step comprising ammonium sulfate precipitation and affinity column chromatography.

A reaction solution having the composition shown in Table 1 of Example 1, and a reaction solution having the composition shown in Table 1, to which XerCD was added to a final concentration of 3.5 nM, 7 nM, 14 nM, or 35 nM, were prepared. To each of these reaction solutions, template DNA or control DNA was added to a final concentration of 0.8 ng/µl, and they were then mixed with each other on ice. Thereafter, the obtained mixture was incubated in an incubator at 30° C. for 1 hour for reaction. The total volume for a single reaction was set at 10 microliter. To the reaction solution, [α-$^{32}$P]dATP had been added, and after completion of the reaction, a by-product was detected in the same manner as that of Example 1. Thereafter, the structure thereof was confirmed.

<Results>

The detection result of a replication product is shown in FIG. 4(b).

It could be confirmed that, when a dif-inserted 12-kb circular DNA was used as a template and XerCD was comprised in the reaction solution, circular DNA having a supercoiled structure of interest was replicated or amplified, while suppressing generation of a multimer as a by-product. On the other hand, when the 8.0-kb circular DNA not comprising a dif sequence was used as a template and the reaction solution did not comprise XerCD, generation of circular DNA having a supercoiled structure of interest was observed, but at the same time, generation of a multimer as a by-product was also observed.

The XerCD-dif system is a mechanism of conducting chromosome disjunction in a circular chromosome. That is, the XerCD-dif system is a mechanism of conducting separation of a DNA multimer. According to the experimental results shown in the present example, it was confirmed that generation of a non-specific DNA multimer can be suppressed by incorporating this system into a reaction of replicating or amplifying circular DNA.

Example 3: Influence of Position of Ter Sequence or Dif Sequence in Circular DNA In Examples 1 and 2, template DNA was prepared such that the ter sequence or the dif sequence was positioned in a region opposite to oriC in the circular DNA. In Example 3, a replication and/or amplification reaction was carried out on circular DNA, in which the ter sequence or the dif sequence was disposed in a position close to or adjacent to oriC.

<Materials and Methods>

In order to construct 15-kb circular DNA, using *Escherichia coli* genome as a template, a 15-kb DNA fragment not comprising oriC was amplified and prepared.

As circular DNA in which the ter sequences were disposed close to oriC, 15 kb ori-ter circular DNA was prepared as follows. An ori-ter cassette was connected with the above described 15-kb DNA fragment, followed by circularization, to produce the ori-ter circular DNA (FIG. 5). The sequence of the ori-ter cassette (0.38 kb) was as follows, and the ter sequences facing outward (underlined portions) were present at both termini of the oriC cassette (small letters).

ori-ter cassette:

(SEQ ID NO: 27)
5'-<u>AGTATGTTGTAACTAAAG</u>ATAACTTCGTATAATGTATGCTATACGAA

GTTATacagatcgtgcgatctactgtggataactctgtcaggaagcagga tcaaccggtagttatccaaagaacaactgagttcagatttgagagtgtat aacccctcattctgatcccagcttatacggtccaggatcaccgatcattc acagttaatgatcattccaggagagatcttaaaagccggatccttgttat ccacagggcagtgcgatcctaataagagatcacaatagaacagatctcta aataaatagatcactattaatacccaggatccATTTAACATAATATACAT TATGCGCAC<u>CTTTAGTTACAACATACT</u>-3'

As circular DNA in which the dif sequence was disposed close to oriC, 15 kb ori-dif circular DNA was prepared as follows. An ori-dif cassette was connected with the above described 15-kb DNA fragment, followed by circularization, to produce the ori-dif circular DNA (FIG. 5). The sequence of the ori-dif cassette (0.32 kb) was as follows, and the dif sequence (underlined portion) was present adjacent to the side upstream of the oriC cassette (small letters).

ori-dif cassette:

(SEQ ID NO: 28)
5'-<u>ATTTAACATAATATACATTATGCGCACC</u>AAGTATacagatcgtgcga tctactgtggataactctgtcaggaagcaggatcaaccggtagttatcca aagaacaactgagttcagatttgagagtgtataaccccctcattctgatcc cagcttatacggtccaggatcaccgatcattcacagttaatgatcctttc caggttgttgatcttaaaagccggatccttgttatccacagggcagtgcg atcctaataagagatcacaatagaacagatctctaaataaatagatcact attaatacccaggatcc-3'

In order to study suppression of generation of a DNA multimer that was dependent on ter and Tus, Tus was added to a reaction solution with the composition shown in Table 2 below to a final concentration of 0, 2, 6, 20, or 60 nM, and thereafter, circular DNA was added to the reaction mixture to a final concentration to 0.5 ng/µl, 5 pg/µl, 50 fg/µl, or 0.5 fg/µl. The thus obtained mixture was reacted at 30° C. for 3 hours or 17 hours.

In order to study suppression of generation of a DNA multimer by XerCD, XerCD was added to a reaction solution with the composition shown in Table 2 below to a final concentration of 0, 30, or 60 nM, and thereafter, circular DNA was added to the reaction mixture to a final concentration to 0.5 ng/µl. The thus obtained mixture was reacted at 30° C. for 2 hours.

The reaction product was subjected to agarose gel electrophoresis (0.5% 1×TBE, 60 V, 60 minutes), and was then stained with SybrGreen I (Takara Bio Inc.), so that DNA was detected.

TABLE 2

| Reaction buffer | |
|---|---|
| Tris-HCl (pH 8.0) | 20 mM |
| Dithiothreitol | 8 mM |
| Potassium acetate | 150 mM |
| Mg(OAc)$_2$ | 10 mM |
| Creatine phosphate | 4 mM |
| ATP | 1 mM |
| GTP, CTP, UTP | 1 mM each |
| dNTPs | 0.1 mM each |
| tRNA | 50 ng/µL |
| NAD | 0.25 mM |
| Ammonium sulfate | 10 mM |

TABLE 2-continued

| | |
|---|---|
| Bovine serum albumin (BSA) | 0.5 mg/ml |
| Creatine kinase | 20 ng/μL |
| Enzyme group | |
| SSB | 400 nM |
| IHF | 20 nM |
| DnaG | 400 nM |
| DnaN | 40 nM |
| PolIII* | 5 nM |
| DnaB, DnaC | 20 nM |
| DnaA | 100 nM |
| RNaseH | 10 nM |
| Ligase | 50 nM |
| PolI | 50 nM |
| GyrA, GyrB | 50 nM |
| Topo IV | 5 nM |
| Topo III | 50 nM |
| RecQ | 50 nM |

Individual enzymes shown in the table are the same as those described in Example 1, and these enzymes were prepared or acquired by the methods described in Example 1.

Figure 6:
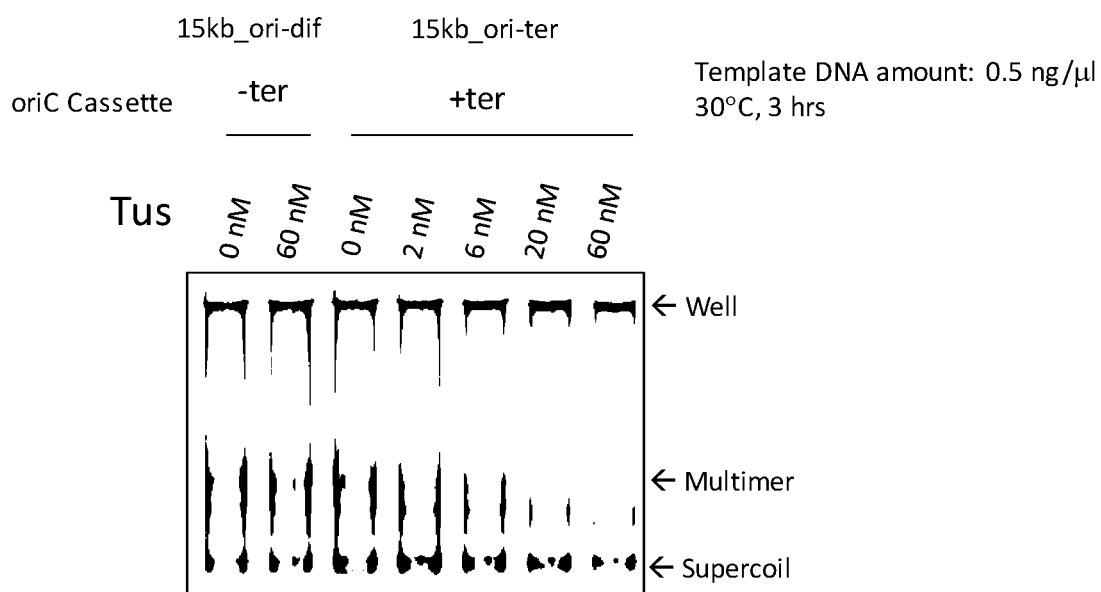
FIG. 6 is a gel electrophoretic photograph showing the result of performing Tus titration regarding suppression of generation of a DNA multimer by utilizing the termination sequence ter and a Tus protein.

<Result 1> Suppression of Generation of DNA Multimer that Depends on Ter and Tus (1) Tus Titration The detection result of a replication/amplification product is shown in FIG. 6. The amount of the template DNA was 0.5 ng/μl, Tus was used in the amount as shown in FIG. 6, and the reaction was carried out at 30° C. for 3 hours.

When the 15 kb ori-ter circular DNA was used as a template and Tus was comprised in the reaction solution, it could be confirmed that circular DNA having a supercoiled structure of interest was replicated or amplified, while suppressing generation of a multimer as a by-product. In addition, as the concentration of Tus in the reaction solution was increased, the effect of suppressing generation of a multimer was increased. Specifically, when Tus was present in a concentration of 20 nM or 60 nM, generation of a multimer was reduced to a level at which generation of the multimer could hardly be confirmed.

On the other hand, when the 15 kb ori-dif circular DNA was used as a template and Tus was comprised in the reaction solution, the effect of suppressing generation of a multimer was not observed. This result shows that the Tus-ter system contributes to the effect of suppressing generation of a multimer.

Moreover, the aforementioned result shows that even in a case where the ter sequences are disposed in positions close to or adjacent to oriC in the circular DNA used as a template, the effect of suppressing generation of a multimer is obtained. That is to say, the positions of the ter sequences inserted into the circular DNA do not have influence on the effect of suppressing generation of a multimer.

(2) DNA Titration

Figure 7:
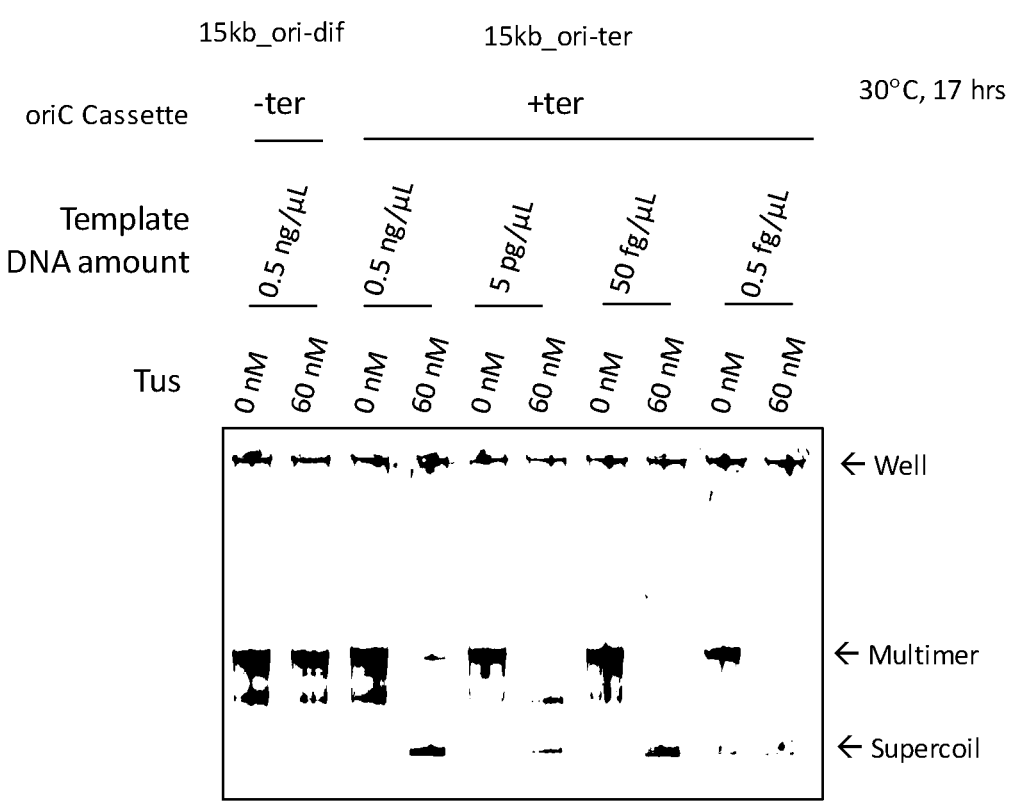
FIG. 7 is a gel electrophoretic photograph showing the result of performing DNA titration regarding suppression of generation of a DNA multimer by utilizing the termination sequence ter and a Tus protein.

The detection result of a replication/amplification product is shown in FIG. 7. The template DNA and Tus were used in each amount as shown in FIG. 7, and the reaction was carried out at 30° C. for 17 hours.

When the 15 kb ori-ter circular DNA was used as a template and Tus was comprised in the reaction solution, it could be confirmed that circular DNA having a supercoiled structure of interest was replicated or amplified, while suppressing generation of a multimer as a by-product. In particular, it was confirmed that even though the amount of the template DNA was reduced to 0.5 fg/μl, this effect could be observed.

<Result 2> Suppression of Generation of DNA Multimer by XerCD

Figure 8:
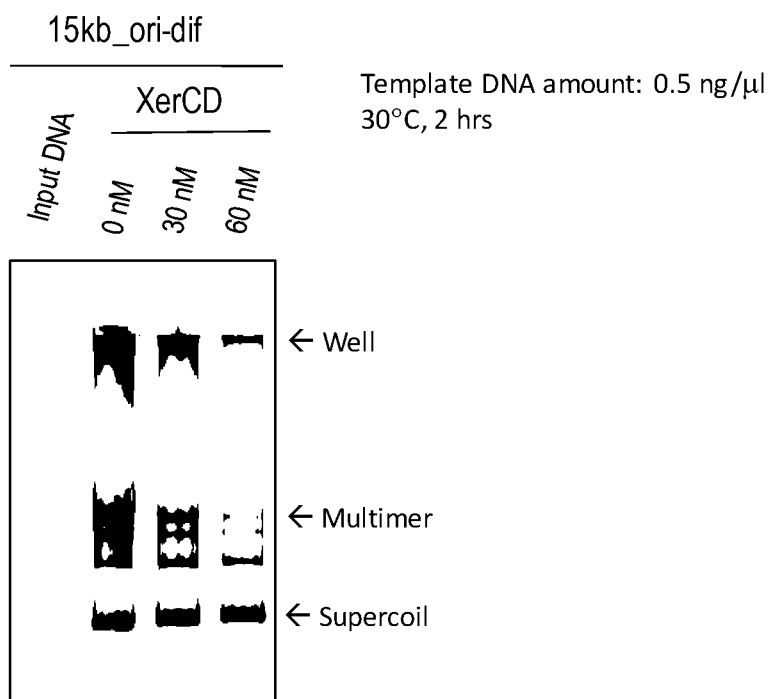
FIG. 8 is a gel electrophoretic photograph showing the result of suppression of generation of a DNA multimer by XerCD.

The detection result of a replication/amplification product is shown in FIG. 8. The amount of the template DNA was 0.5 ng/μl, XerCD was used in the amount as shown in FIG. 8, and the reaction was carried out at 30° C. for 2 hours.

When the 15 kb ori-dif circular DNA was used as a template and XerCD was comprised in the reaction solution, it could be confirmed that circular DNA having a supercoiled structure of interest was replicated or amplified, while suppressing generation of a multimer as a by-product. In addition, as the concentration of XerCD in the reaction solution was increased, the effect of suppressing generation of a multimer was increased.

Moreover, the aforementioned result shows that even in a case where the dif sequence is disposed in a position close to or adjacent to oriC in the circular DNA used as a template, the effect of suppressing generation of a multimer is obtained. That is to say, the position of the dif sequence inserted into the circular DNA does not have influence on the effect of suppressing generation of a multimer.

From the aforementioned results 1 and 2, it was found that even in a case where the ter sequences and the dif sequence were disposed close to or adjacent to oriC, the sequences efficiently functioned and suppressed generation of a DNA multimer. The ter sequences and the dif sequence that can be disposed close to oriC mean that these sequences, together with oriC, can be utilized as a functional cassette in construction of circular DNA.

Example 4: Introduction of oriC Cassette by Utilizing Transposon (1)

In order to replicate or amplify circular DNA according to the method of the present application, oriC needs to be introduced into the circular DNA used as a template. In Example 4, introduction of an oriC cassette by utilizing a transposon was studied (FIG. 2).

<Materials and Methods>

As a transposase (Tnp), a highly active Tn5 mutant (E54K, L372P) protein was used. This protein was prepared by purifying it from an *Escherichia coli* strain expressing it according to a step comprising ammonium sulfate precipitation and affinity column chromatography.

As an oriC transposon, a DNA fragment consisting of the following sequence, in which outside end (OE) sequences (underlined portions) are present at both termini of a sequence comprising oriC, which was then 5'-phosphorylated, was used.

oriC transposon:

(SEQ ID NO: 29)
5'-<u>CTGTCTCTTATACACATCT</u>gaagatccggcagaagaatggctgggat cgtgggttaatttactcaaataagtatacagatcgtgcgatctactgtgg ataactctgtcaggaagcaggatcaaccggtagttatccaaagaacaact gagttcagatttgagagtgtataacccctcattctgatcccagcttatac ggtccaggatcaccgatcattcacagttaatgatccatccaggagagatc ttaaaagccggatccagttatccacagggcagtgcgatcctaataagaga tcacaatagaacagatctctaaataaatagatcactattaatacccagga tcccaggtctactcaagccgac<u>AGATGTGTATAAGAGACAG</u>-3'

The oriC transfer reaction was carried out by incubating 116 nM Tnp and 48 nM oriC transposon in a buffer (10 mM Tris-acetic acid [pH 7.5], 15% glycerol, 50 mM potassium glutamate, 1 mM DTT, and 0.1 mM EDTA) at 30° C. for 30 minutes, thereby obtaining an oriC transposome. The oriC transposome (0.5 μl) and target DNA (10 fM) were incubated in a buffer (5 μl; 10 mM Tris-HCl [pH 7.5], 150 mM potassium glutamate, and 10 mM Mg(oAc)$_2$) at 37° C. for 15 minutes to perform a transfer reaction. As such target DNA, a 15-kb *Escherichia coli* gene expression plasmid (pTT8 plasmid), or a 9.3-kb plasmid extracted from a high thermophile *Thermus thermophilus* HB8 strain was used. Thereafter, a heat inactivation treatment was carried out at 70° C. for 5 minutes.

An aliquot (0.5 μl) of the reaction mixture obtained from the above described oriC transfer reaction was added to the reaction solution with the composition shown in Table 2 of Example 3, and the thus obtained mixture was then reacted at 30° C. for 3 hours. The reaction product was subjected to agarose gel electrophoresis (0.5% 1×TBE, 60 V, 60 minutes), and was then stained with SybrGreen (Takara Bio Inc.), so that DNA was detected.

<Results>

Figure 9:
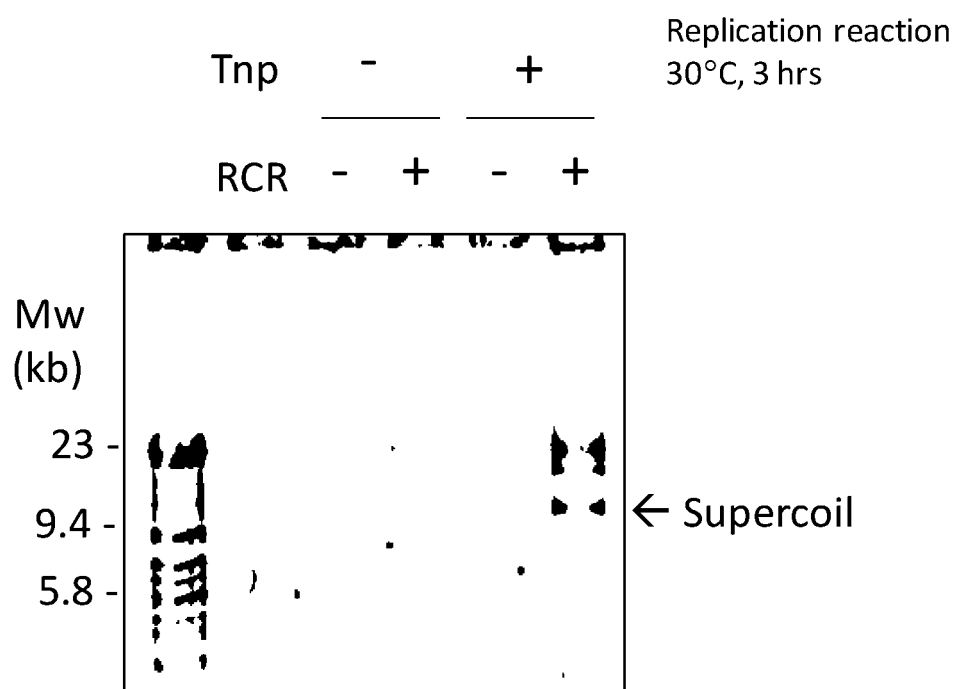
FIG. 9 is a gel electrophoretic photograph showing the result of amplification of a 15-kb plasmid by oriC transposon transfer.
Figure 10:
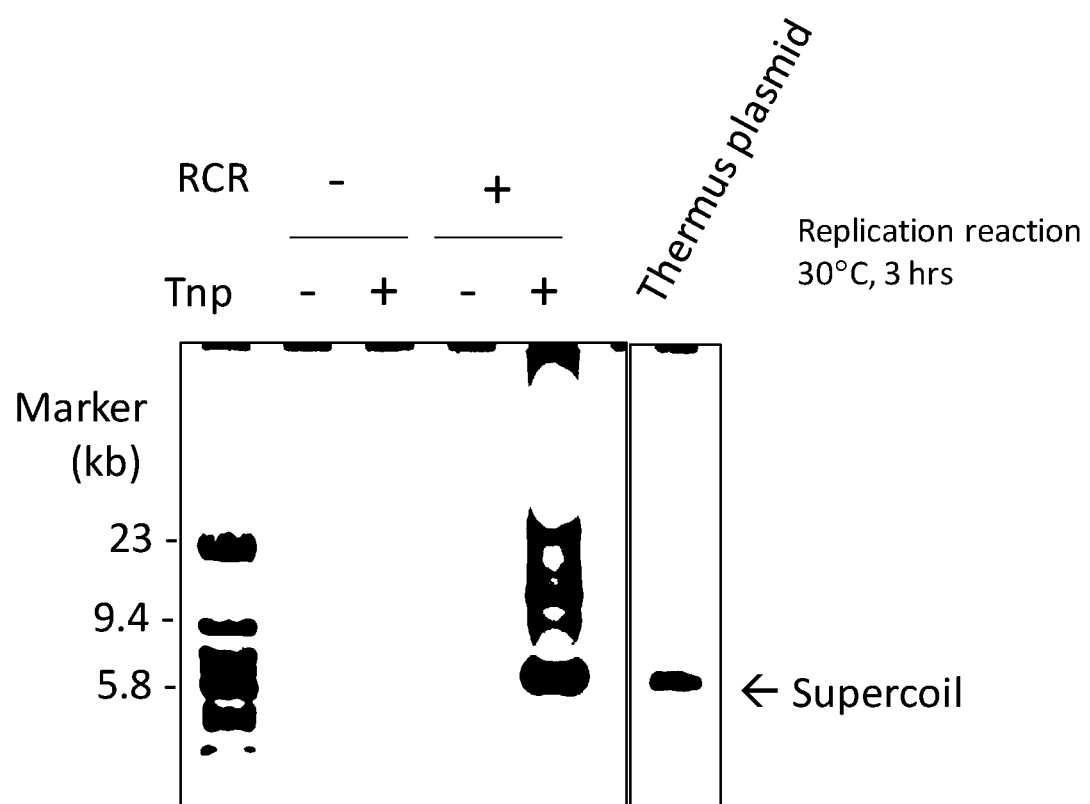
FIG. 10 is a gel electrophoretic photograph showing the result of amplification of a thermophile-derived 9.3-kb plasmid with a high GC content rate by oriC transposon transfer.

The result obtained in the case of using the 15-kb *Escherichia coli* gene expression plasmid as target DNA is shown in FIG. 9, and the result obtained in the case of using the 9.3-kb plasmid (pTT8 plasmid) extracted from a high thermophile *Thermus thermophilus* HB8 strain as target DNA is shown in FIG. 10.

When an aliquot of the reaction mixture obtained from the oriC transfer reaction, in which Tnp was present, was used in the method for replicating or amplifying circular DNA, a supercoil that was a replication product/amplification product was found. On the other hand, when Tnp was not present in the oriC transfer reaction, such a replication product/amplification product was not found, even after the method for replicating or amplifying circular DNA had been carried out.

Moreover, the aforementioned result shows that oriC could be efficiently introduced into target DNA, in particular, in an extremely low concentration that was 10 fM (0.1 pg/μl), and that the target DNA could be amplified according to the method for replicating or amplifying circular DNA of the present application. This result shows that introduction of oriC into the target DNA can be easily achieved with high efficiency by utilizing a transposon for an oriC cassette, and that the thus obtained circular DNA comprising oriC can also be efficiently amplified according to the method for replicating or amplifying circular DNA of the present application.

Example 5: Introduction of oriC Cassette by Utilizing Transposon (2)

The same transposase (Tnp) and oriC transposon as those in Example 4 were used.

The oriC transfer reaction was carried out by incubating 116 nM Tnp and 144 nM oriC transposon in a buffer (10 mM Tris-acetic acid [pH 7.5], 15% glycerol, 50 mM potassium glutamate, 1 mM DTT, and 0.1 mM EDTA) at 30° C. for 30 minutes, thereby obtaining an oriC transposome. The oriC transposome (0.5 μl), target DNA (1 pM (50 pg (3×10$^6$ molecules)/5 μl), and tRNA (50 ng/μl) were incubated in a buffer (5 μl; 10 mM Tris-HCl [pH 7.5], 150 mM potassium glutamate, and 10 mM Mg(oAc)$_2$) at 37° C. for 15 minutes to perform a transfer reaction. As such target DNA, a 15-kb *Escherichia coli* gene expression plasmid was used. Thereafter, a heat inactivation treatment was carried out at 70° C. for 5 minutes.

Figure 11:
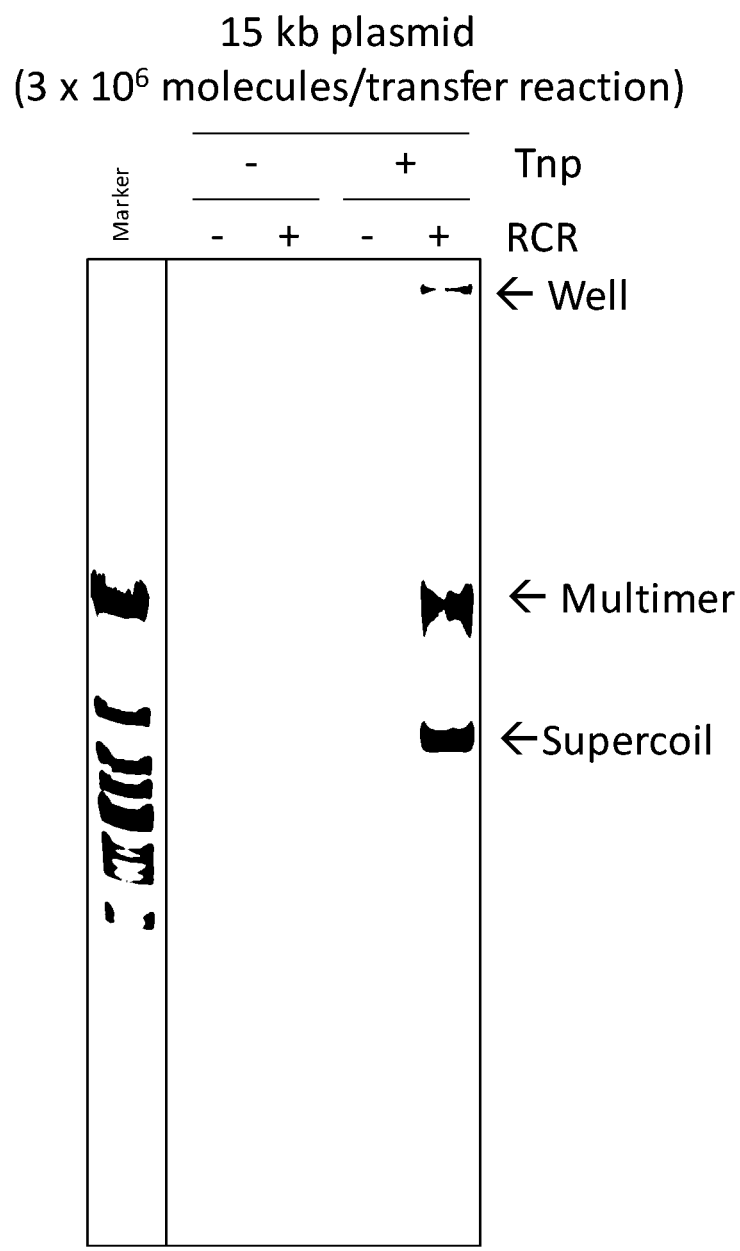
FIG. 11 is a gel electrophoretic photograph showing the result of amplification of a 15-kb plasmid by oriC transposon transfer.

An aliquot (0.5 μl) of the reaction mixture obtained from the above described oriC transfer reaction was added to 5 μl of the reaction solution with the composition shown in Table 2 of Example 3, and the thus obtained mixture was then reacted at 30° C. for 4 hours. The reaction product was subjected to agarose gel electrophoresis (0.5% 1×TBE, 60 V, 55 minutes), and was then stained with SybrGreen I (Takara Bio Inc.), so that DNA was detected. The result is shown in FIG. 11. As with Example 4, when an aliquot of the reaction mixture obtained from the oriC transfer reaction, in which Tnp was present, was used in the reaction of replicating or amplifying circular DNA, a supercoil that was a replication product/amplification product was found. On the other hand, when Tnp was not present in the oriC transfer reaction, such a replication product/amplification product was not found, even after the reaction of replicating or amplifying circular DNA had been carried out.

Figure 12:
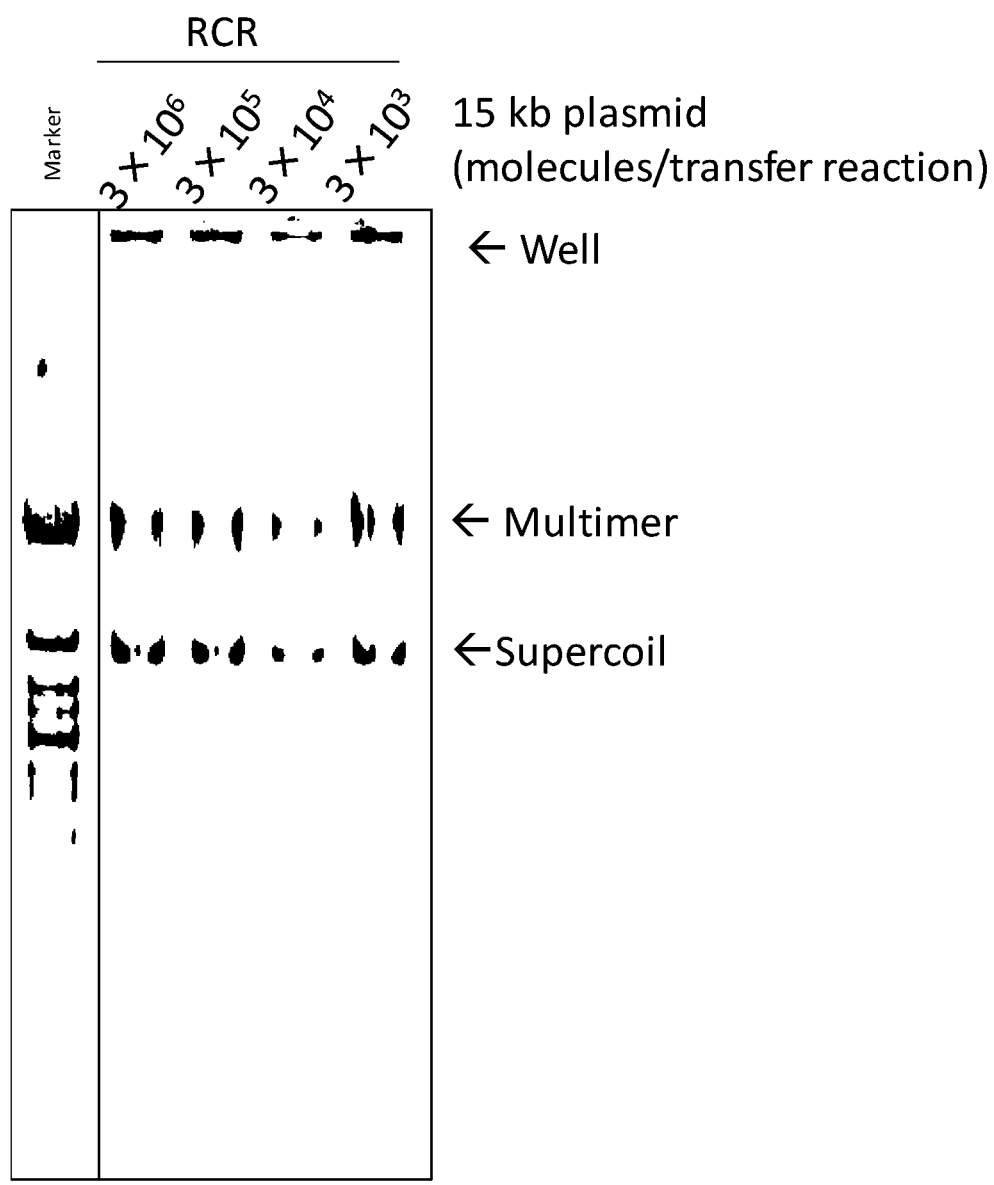
FIG. 12 is a gel electrophoretic photograph showing the result of amplification of a 15-kb plasmid by oriC transposon transfer, in a case where the amount of DNA used in the oriC transposon transfer reaction is changed.

Furthermore, the additive amount of the target DNA in the oriC transfer reaction was changed to 1 pM (50 pg (3×10$^6$ molecules)/5 μl), 0.1 pM (5 pg (3×10$^5$ molecules)/5 μl), 10 fM (500 fg (3×10$^4$ molecules)/5 μl), and 1 fM (50 fg (3×10$^3$ molecules)/5 μl), and the same reaction as that described above was carried out. The result is shown in FIG. 12. The result shows that oriC could be efficiently introduced into the target DNA in an extremely low concentration that was 1 fM (50 fg (3000 molecules)/5 μl), and that the target DNA could be amplified according to the method for replicating or amplifying circular DNA of the present application.

Example 6—Amplification of Thermophile Plasmid by oriC Transposon Transfer

Figure 13:
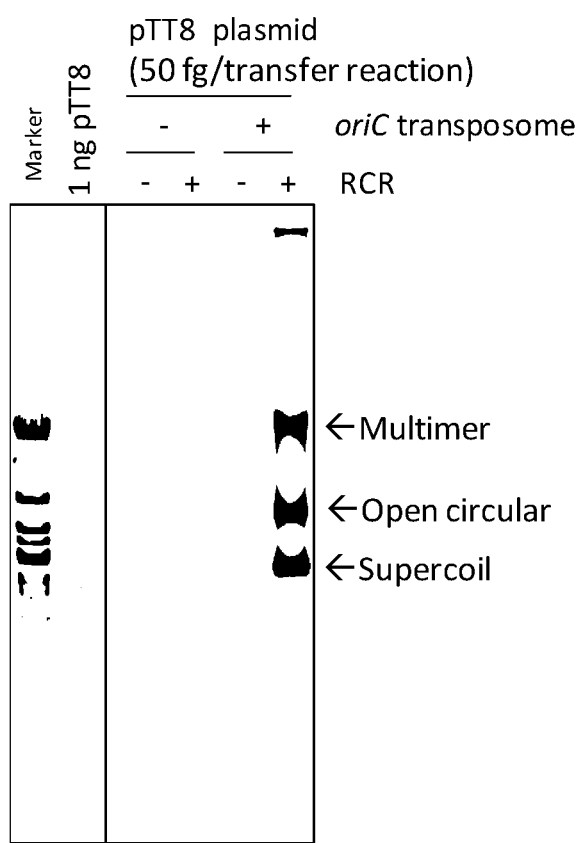
FIG. 13 is a gel electrophoretic photograph showing the result of amplification of a thermophile-derived 9.3-kb plasmid with a high GC content rate by oriC transposon transfer.

The oriC transfer reaction and the reaction of replicating or amplifying circular DNA were carried out in the same manner as that in Example 5, with the exception that a 9.3-kb plasmid (pTT8 plasmid) extracted from a high thermophile *Thermus thermophilus* HB8 strain was used in an amount of 50 fg as target DNA in the OriC transfer reaction. The result is shown in FIG. 13.

Figure 14:
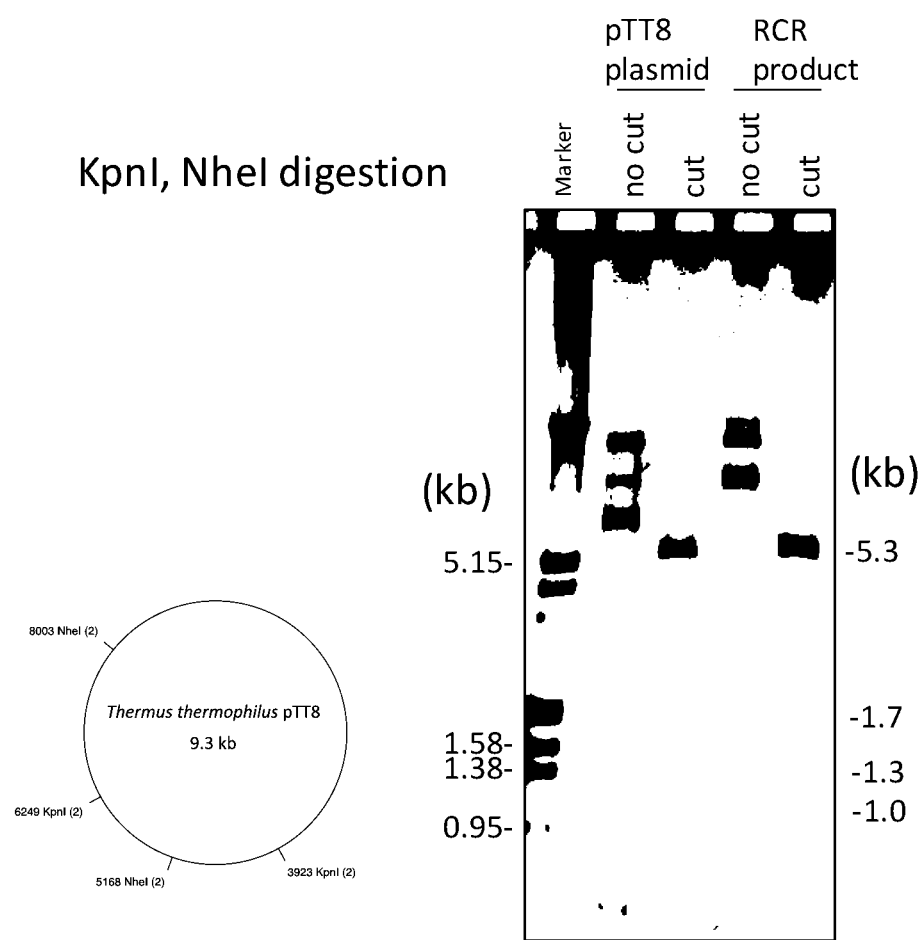
FIG. 14 is a gel electrophoretic photograph showing the result of performing restriction enzyme digestion (KpnI and NheI) on an amplification production of a thermophile-derived 9.3-kb plasmid with a high GC content rate obtained by oriC transposon transfer.

When the pTT8 plasmid is digested with Kpn I and Nhe I, 5.3 kb, 1.7 kb, 1.3 kb and 1.0 kb fragments are generated, as shown in the plasmid map of FIG. 14. The replication product/amplification product obtained by the above described reaction were digested with the restriction enzymes Kpn I and Nhe I. The result is shown in FIG. 14. When the replication product/amplification product obtained by the above described reaction were digested with Kpn I and Nhe I, generation of 5.3 kb, 1.7 kb, 1.3 kb, and 1.0 kb fragments was confirmed, as in the case of the pTT8 plasmid. This result shows that the replication product/amplification product obtained by the above described reaction is circular DNA, which was obtained by performing oriC transposon transfer on the pTT8 plasmid, and then replicating and/or amplifying the resultant.

These results show that, even in the case of using a 9.3-kb plasmid with a high GC content percentage (GC content percentage: approximately 70%), which was derived from heterologous cells, oriC could be efficiently introduced into target DNA in an extremely low concentration, as with Example 5, and the target DNA could be amplified according to the method for replicating or amplifying circular DNA of the present application.

Example 7: Amplification of λDNA by oriC Transposon Transfer

λDNA is bacteriophage-derived linear DNA. This DNA was circularized, and oriC was then introduced therein by oriC transposon transfer, thereby preparing circular DNA. Thereafter, the method for replicating or amplifying circular DNA of the present application was carried out on the circular DNA.

(1) Annealing and Gap Repair Reaction

An annealing reaction was carried out as follows. 160 ng/μl λDNA (48 kb/Toyobo Co., Ltd.) was added into a buffer (10 mM Tris-HCL (pH 7.5), 50 mM NaCl, and 1 mM EDTA) to obtain 5 μl of solution. This solution was incubated at 65° C. for 5 minutes, and was then cooled to 4° C. at a temperature-decreasing rate of −0.5° C./30 sec, and the COS sites at both termini of the λDNA were connected with each other for circularization.

A gap repair reaction was carried out as follows. After completion of the annealing reaction, 0.5 μl of the obtained solution was added to a reaction solution comprising 50 nM ligase, 50 nM Pol I, 20 mU/μl Exo III, 5 nM Gyrase, and 0.1 mg/ml BSA (wherein, as a reaction buffer, the reaction buffer with the composition shown in Table 2 was used (i.e., the reaction buffer not comprising the enzyme group shown in Table 2)), and the thus obtained mixture was then reacted at 30° C. for 16 hours.

Figure 15:
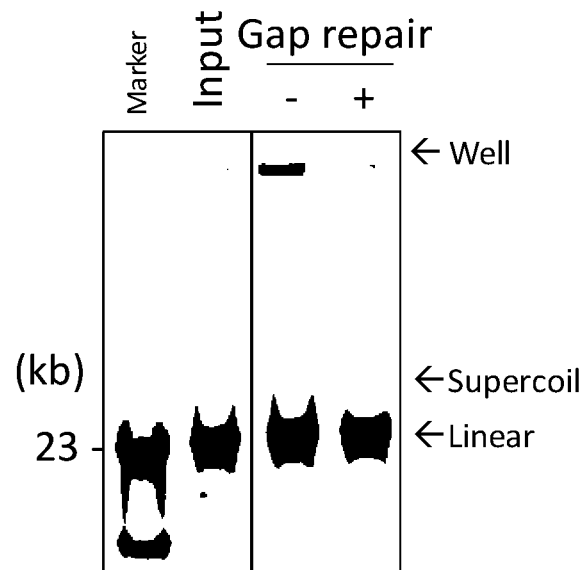
FIG. 15 is a gel electrophoretic photograph showing the result of studying cyclization of λDNA.

The reaction product obtained as a result of the gap repair reaction was subjected to agarose gel electrophoresis (0.5% 1×TBE, 60 V, 55 minutes), and was then stained with SybrGreen I (Takara Bio Inc.), so that DNA was detected. The result is shown in FIG. 15. In the reaction product obtained as a result of the gap repair reaction, a band of a supercoil showing the presence of circularized DNA with no gaps was observed.

(2) oriC Transposon Transfer and Amplification of λDNA

Figure 16:
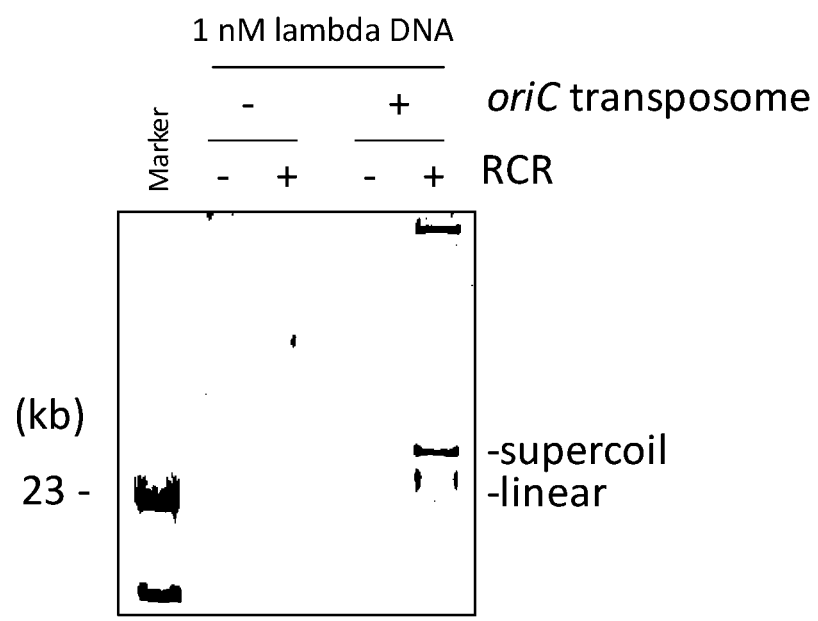
FIG. 16 is a gel electrophoretic photograph showing the result of cyclization of λDNA and amplification of circular DNA by oriC transposon transfer.

The reaction product (1 μl) obtained as a result of the gap repair reaction was used as a solution comprising target DNA, the oriC transfer reaction and the reaction of replicating or amplifying circular DNA were carried out in the same manner as that in Example 5. Herein, for the reaction of replicating or amplifying circular DNA, the reaction solution with the composition shown in Table 2 of Example 3, to which 60 nM RecG and 0.5 U/μl RecJf (NEB) were further added, was used. RecG was prepared by generating it from a RecG-expressing *Escherichia coli* strain according to a step comprising ammonium sulfate precipitation and affinity column chromatography. The result is shown in FIG. 16.

Figure 17:
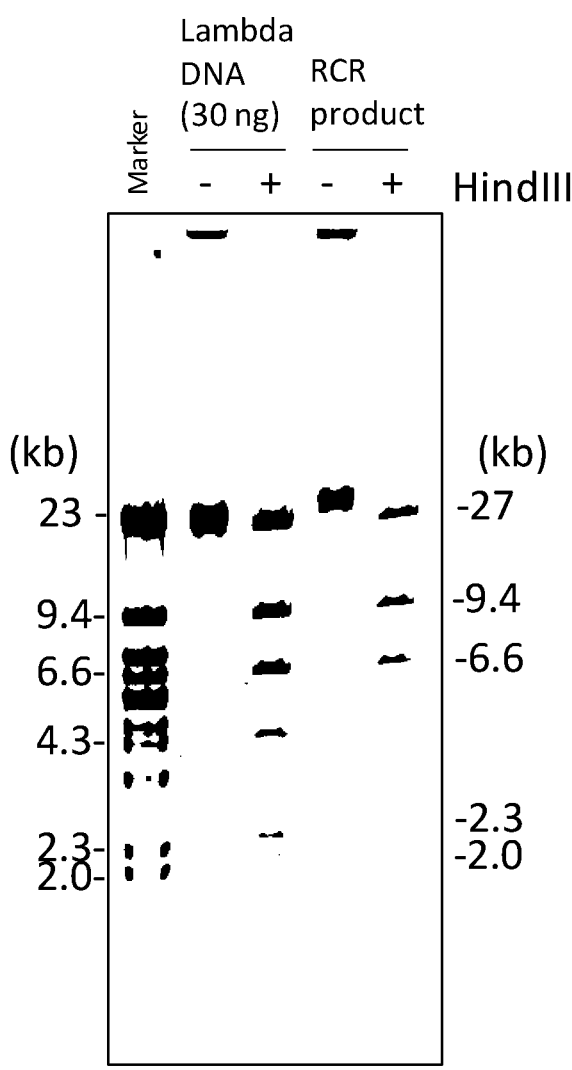
FIG. 17 is a gel electrophoretic photograph showing the result of cyclization of λDNA and restriction enzyme digestion (HindIII) performed on an amplification product of circular DNA prepared by oriC transposon transfer.

When the λDNA is digested with the restriction enzyme HindIII, 27 kb, 9.4 kb, 6.6 kb, 2.3 kb and 2.0 kb fragments are generated. The replication product/amplification product obtained by the above described reaction were digested with the restriction enzyme HindIII (37° C., 3 hours). The result is shown in FIG. 17. When the replication product/amplification product obtained by the above described reaction were digested with HindIII, 7 kb, 9.4 kb, 6.6 kb, 2.3 kb and 2.0 kb fragments were confirmed, as in the case of the λDNA. This result shows that the replication product/amplification product obtained by the above described reaction is circular DNA, which was obtained by performing oriC transposon transfer on circularized λDNA, and then replicating and/or amplifying the resulting λDNA.

These results show that, even in the case of linear DNA, the reaction of replicating or amplifying circular DNA of the present application can be utilized by performing an oriC transfer reaction after circularization of the linear DNA.

Example 8: Removal of oriC Transposon (1)

Whether or not the oriC introduced into circular DNA according to an oriC transfer reaction can be removed was studied.

(1) Circular DNA

The oriC transposon of Example 5 comprises a kanamycin (Km) resistance gene and oriC. On the other hand, a 15-kb *Escherichia coli* gene expression plasmid comprises an ampicillin (Amp) resistance gene. Circular DNA (referred to as "p15k::Km-oriC"), in which an oriC transposon had been transferred into a region encoding the ampicillin resistance gene of a 15-kb *Escherichia coli* gene expression plasmid, among the plasmids obtained by the oriC transfer reaction of Example 5, was selected and recovered. Specifically, the plasmids obtained by the oriC transfer reaction of Example 5 were transformed into *Escherichia coli*, and the transformants, which became sensitive to Amp and resistant to Km, were cloned by screening.

(2) Dissociation of oriC Transposon

Figure 18:
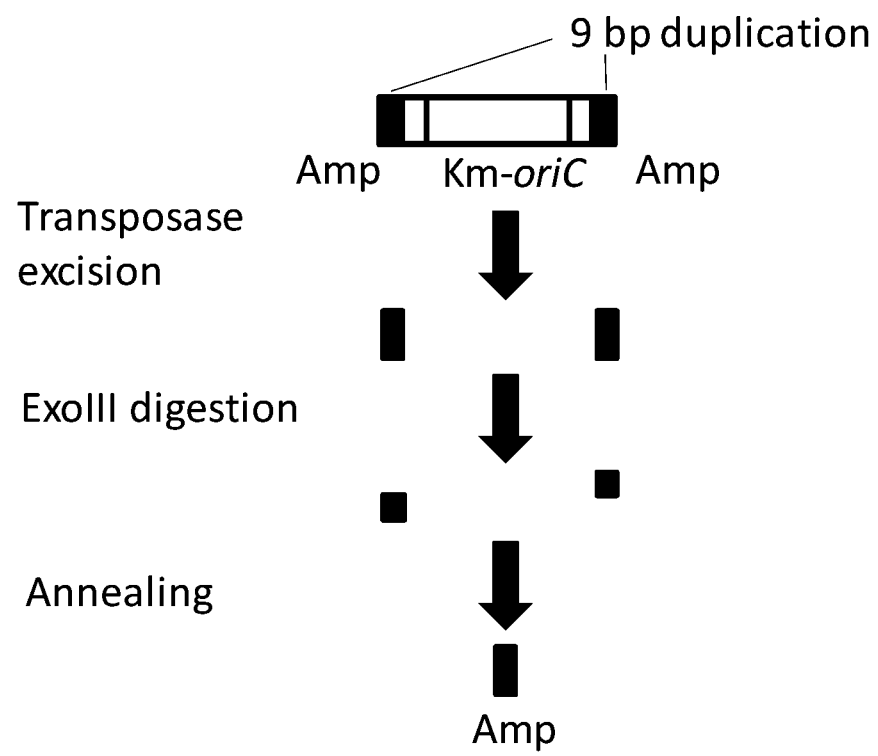
FIG. 18 is a schematic view showing the dissociation reaction of an oriC transposon.

The region corresponding to the oriC transposon transferred by the oriC transfer reaction is dissociated using transposase. In addition, 9-bp regions are duplicatedly formed on both termini of the oriC transposon when the oriC transposon is transferred by the oriC transfer reaction. Thus, upon the removal of the oriC transposon, it is necessary to treat these 9-bp regions after completion of the connection, so that the regions cannot be duplicatedly present. The DNA terminus comprising the 9-bp region, which was generated by extraction of the oriC transposon, was converted to a single-stranded terminus by using ExoIII that was straight-chain double-stranded DNA dependent single-stranded DNA exonuclease. Thereafter, by utilizing the duplicated portion of 9-bp regions, single strands were annealed to each other and were circularized. FIG. 18 shows a schematic view thereof.

Specifically, the following reaction was carried out.

The oriC transposon dissociation reaction was carried out by incubating 0 to 30 nM (0 nM, 3 nM, 10 nM and 30 nM) transposase and 2 ng/μl p15k::Km-oriC in a buffer (5 μl; 10 mM Tris-HCl [pH 7.5], 150 mM potassium glutamate, and 10 mM Mg(oAc)$_2$) at 37° C. for 16 hours. Thereafter, a heat inactivation treatment was carried out at 70° C. for 5 minutes.

Takara ExoIII buffer (50 mM Tris-HCl (pH 8.0), 5 mM MgCl$_2$, and 1 mM DTT) and 20 mU/μl ExoIII (Takara) were added to 1 μl of the oriC transposon dissociation reaction product to result in a final volume of 5 μl. This mixture was reacted at 30° C. for 10 minutes, so that it was treated with ExoIII.

The reaction product treated with ExoIII was incubated at 65° C. for 5 minutes, and was then cooled to 4° C. at a temperature decreasing rate of −0.5° C./30 sec to perform annealing.

(3) Confirmation of Dissociation of oriC transposon by transformation

*Escherichia coli* was transformed using 2 μl of the sample obtained in the above (2) and chemical competent cells (*Escherichia coli* DH5α) 50. The transformed cells were seeded on a plate including 100 μg/ml ampicillin, 25 μg/ml-kanamycin, and were then incubated at 37° C. overnight.

The colony formation when transposase was not added in the above (2) (0 nM) was set at 100, and the relative colony formation unit (%) when the concentration of transposase was changed was then calculated.

(4) Results

Figure 19:
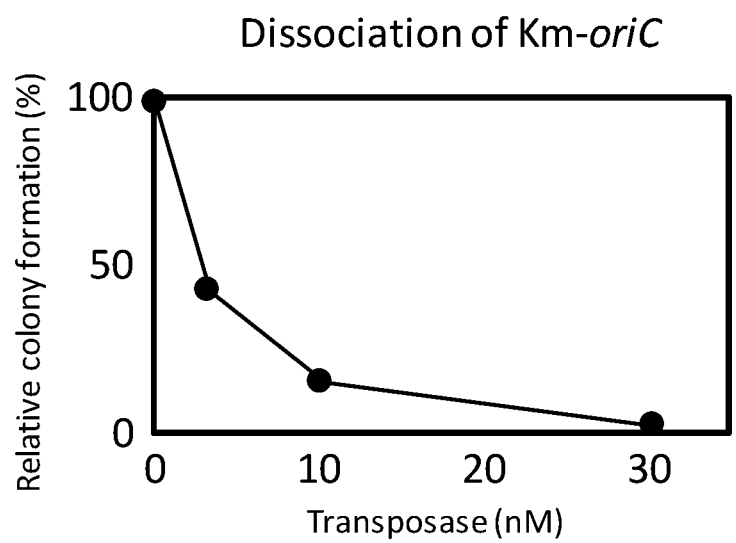
FIG. 19 is a graph showing evaluation of the dissociation of an oriC transposon comprising Km-oriC.
Figure 20:
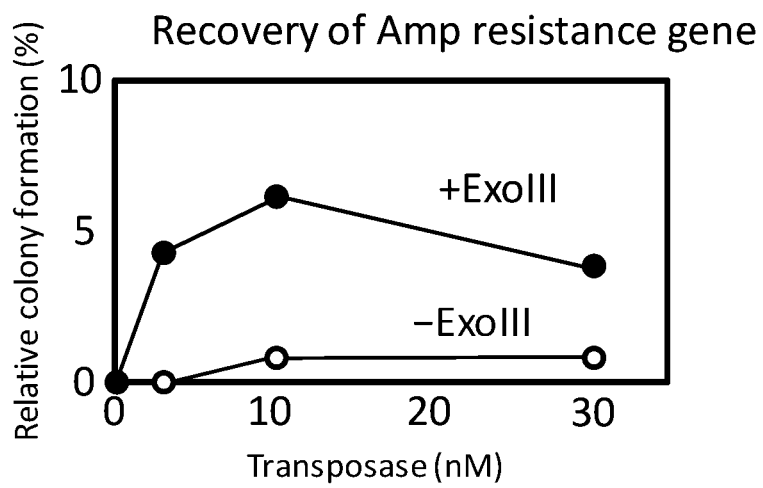
FIG. 20 is a graph showing evaluation of an Amp resistance gene recovered after the dissociation of an oriC transposon.

The results are shown in FIG. 19 and FIG. 20.

From the result shown in FIG. 19, it became clear that the kanamycin resistance transformed cells were reduced depending on the concentration of the added transposase. When 30 nM transposase was added, almost no kanamycin resistance transformed cells were present. This result shows that the oriC transposon can be dissociated by addition of transposase.

In addition, from the result shown in FIG. 20, it became clear that once destructed ampicillin gene could be returned by insertion of the oriC transposon, depending on the ExoIII treatment.

Example 9: Removal of oriC Transposon (2)

Figure 21:
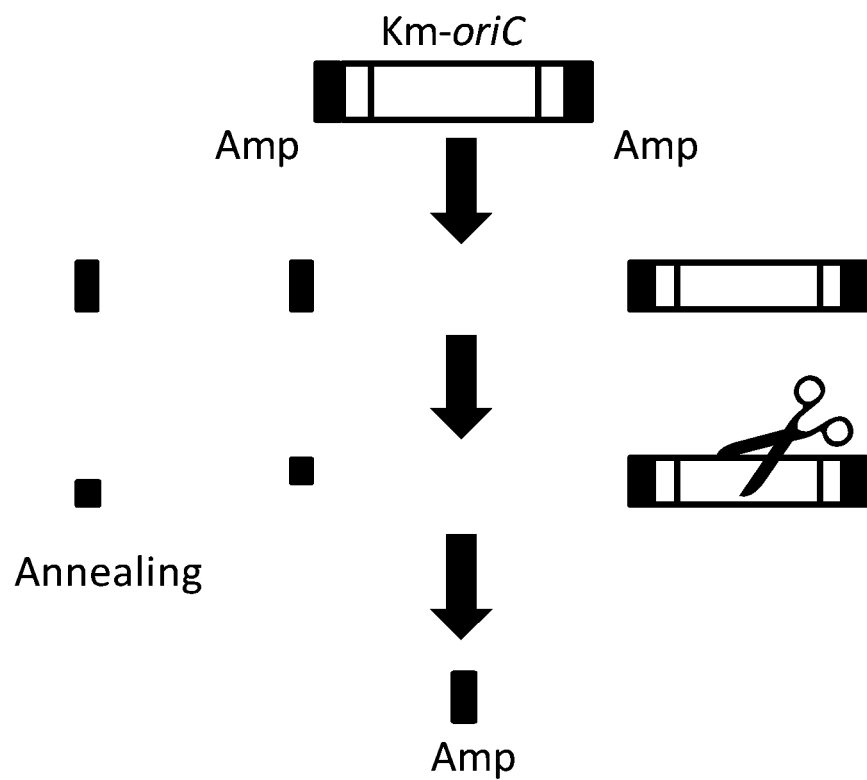
FIG. 21 is a schematic view showing the dissociation reaction of an oriC transposon and the removal reaction of the oriC transposon by cleavage.

The removal of the oriC transposon by performing a treatment using a restriction enzyme corresponding to the restriction enzyme site comprised in the sequence of the oriC transposon, in parallel with performing an ExoIII treatment, was studied. FIG. 21 shows a schematic view thereof.

(1) Circular DNA

The same circular DNA as that of Example 8 was used.

(2) Dissociation of oriC Transposon

The oriC transposon dissociation reaction was carried out in the same manner as that in Example 8 with the exception of the use of 10 nM transposase.

Takara ExoIII buffer (50 mM Tris-HCl (pH 8.0), 5 mM $MgCl_2$, and 1 mM DTT), and 20 mU/µl ExoIII (Takara) alone, or 20 mU/µl ExoIII (Takara) and 0.6 U/µl NheI (NEB), were added to 1 µl of the oriC transposon dissociation reaction product, so as to result in a final volume of 5 µl. This mixture was reacted at 30° C. for 10 minutes, so as to perform an ExoIII treatment.

The reaction product treated with ExoIII and NheI was incubated at 65° C. for 5 minutes, and was then cooled to 4° C. at a temperature decreasing rate of −0.5° C./30 sec to perform annealing.

(3) Confirmation of Dissociation of oriC Transposon by Transformation

Transformation was carried out in the same manner as that in Example 8.

Thereafter, the colony formation unit was calculated.

(4) Result

The result is shown in Table 3

TABLE 3

| | Colony formation unit | |
|---|---|---|
| | Amp resistance | Km resistance |
| ExoIII+/NheI− | 155 | 75 |
| ExoIII+/NheI+ | 157 | 20 |

This result shows that the problem that a plasmid containing transposons that has not been dissociated from the circular DNA even by using transposase remains as a background can be reduced by cleaving the transposon DNA site with the restriction enzyme (NheI).

Example 10: Suppression of Generation of DNA Multimer by Cre

<Materials and Methods>

Using pUC19 (Takara Bio Inc.) as a template, PCR was carried out with the primers SUE1156: 5'-CTATGCGG-CATCAGAGCAG-3' (SEQ ID NO: 38) and SUE1361: 5'-GTTAAGCCAGCCCCGACAC-3' (SEQ ID NO: 39), so as to prepare a 2.6-kb pUC DNA fragment.

As circular DNA in which a loxP sequence was disposed in a position close to oriC, pUC19-OLDT circular DNA was prepared as follows. A pUC DNA fragment was connected with an OLDT cassette for circularization, thereby producing the pUC19-OLDT circular DNA. The sequence of the OLDT cassette (0.41 kb) is as follows, and the OLDT cassette has a loxP sequence (underlined portion) adjacent to the side upstream of the oriC cassette (small letter portion).

OLDT cassette:

(SEQ ID NO: 40)
5'-CGCGTCAGCGGGTGTTGGCGGGTGTCGGGGCTGGCTTAACAGTATGT

TGTAACTAAAGATAACTTCGTATAATGTATGCTATACGAAGTTATACAGA

TCGTGCgatctactgtggataactctgtcaggaagcaggatcaaccggta gttatccaaagaacaactgagttcagatttgagagtgtataacccctcat tctgatcccagcttatacggtccaggatcaccgatcattcacagttaatg atcattccaggagagatcttaaaagccggatccagttatccacagggcag tgcgatcctaataagagatcacaatagaacagatctctaaataaatagat cttcttttaatacCCAGGATCCATTTAACATAATATACATTATGCGCAC

CTTTAGTTACAACATACTATGCGGCATCAGAGCAGATTGTACTGAGAGTG

CACCAT-3'

As control circular DNA not having such a loxP sequence, pUC-OriC300 circular DNA was prepared as follows. A pUC DNA fragment was connected with an oriC300 cassette for circularization, thereby producing the pUC-oriC 300 circular DNA. The sequence of the oriC 300 cassette (0.41 kb) is as follows, and the oriC 300 cassette has an oriC cassette (small letter portion).

oriC 300 cassette:
5'-CGCGTCAGCGGGTGTTGGCGGGTGT CGGGGCTGGCTTAACAGTATGTTGTAACTA AAgatc-tactgtggataactctgtcaggaagcttggatcaaccggtagttatc-caaagaacaactgttgttcagtttttgagttgtgtata accccctcattct-gatcccagcttatacggtccaggatcaccgatcattcacagttaatga tccMccaggttgttgatcttaaaagccggat cchgttatccacagggcagtgc-gatcctaataagagatcacaatagaacagatctctaaataaatagatcttctttt-taatacTTTAG TTACAACATACTATGCGG-CATCAGAGCAGATTGTACTGAGAGTGCACCAT-3' (SEQ ID NO: 41)

Cre was purchased from NEB and was used.

A reaction solution with the composition shown in Table 2 of Example 3, and a reaction solution with the composition shown in Table 2 of Example 3, to which Cre had been added to a final concentration of 1 mU/µl, 3 mU/µl, 10 mU/µl or 30 mU/µl, were prepared. To each of these reaction solutions, pUC19-OLDT circular DNA or pUC-OriC300 circular DNA was added to a final concentration of 0.01 ng/µl, and they were then mixed with each other on ice. Thereafter, the obtained mixture was incubated in an incubator at 33° C. for 3 hours for reaction.

The reaction product was subjected to agarose gel electrophoresis (0.5% 1×TBE, 60 V, 60 minutes), and was then stained with SybrGreen I (Takara Bio Inc.), so that DNA was detected.

<Results>

Figure 22:
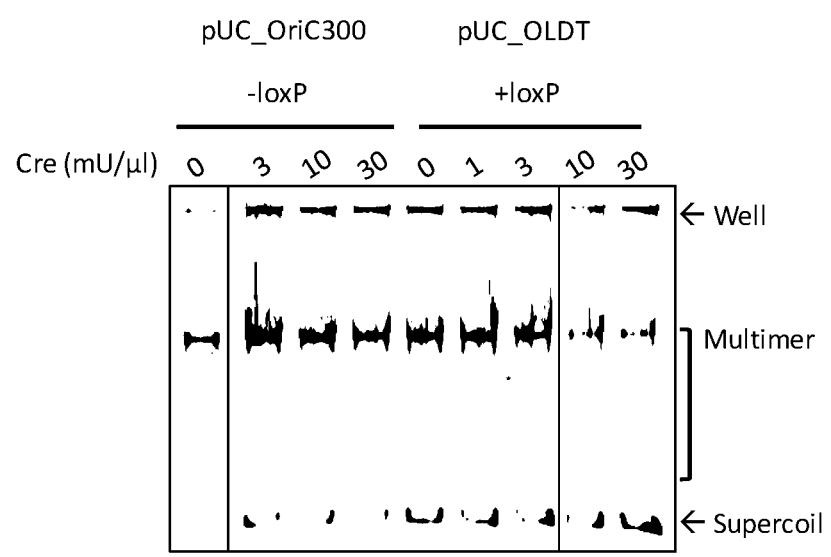
FIG. 22 is a gel electrophoretic photograph showing the result of suppression of generation of a DNA multimer by Cre.

The result of detection of a replication/amplification product is shown in FIG. 22.

It could be confirmed that, when the pUC-OLDT circular DNA in which a loxP sequence was disposed close to oriC was used as a template and Cre was comprised in the reaction solution, circular DNA having a supercoiled structure of interest was replicated or amplified, while suppressing generation of a multimer as a by-product. At this time, the appearance of an intermediate product during separation from a multimer to a monomer was also found. Moreover, by increasing the concentration of Cre in the reaction solution, the effect of suppressing generation of a multimer was increased.

When the pUC19-OriC 300 circular DNA not having a loxP sequence was used as a template, the effects of Cre were not observed.

INDUSTRIAL APPLICABILITY

According to the present invention, there can be provided a method capable of simply and efficiently replicating or amplifying circular DNA, and particularly, long-chain circular DNA.

SEQUENCE LISTING FREE TEXT

SEQ ID NO: 1: ter sequence (consensus)
SEQ ID NO: 2: ter sequence (consensus)
SEQ ID NO: 3: ter sequence (terA, B, D, E, or H)
SEQ ID NO: 4: ter sequence (terA, B, D, E, or H)
SEQ ID NO: 5: ter sequence (terC)
SEQ ID NO: 6: ter sequence (terF)
SEQ ID NO: 7: ter sequence (terG)
SEQ ID NO: 8: ter sequence (terI)
SEQ ID NO: 9: ter sequence (tarJ)
SEQ ID NO: 10: ter sequence (*Bacillus*, consensus)
SEQ ID NO: 11: ter sequence (*Bacillus subtilis*, consensus)
SEQ ID NO: 12: ter sequence (*Bacillus subtilis*, consensus)
SEQ ID NO: 13: ter sequence (terVII)
SEQ ID NO: 14: ter sequence (terIX)
SEQ ID NO: 15: sequence recognized by XerCD (consensus)
SEQ ID NO: 16: sequence recognized by XerCD (consensus, dif and cer)
SEQ ID NO: 17: sequence recognized by XerCD (consensus, dif and psi)
SEQ ID NO: 18: sequence recognized by XerCD (consensus, cer, and psi)
SEQ ID NO: 19: dif sequence
SEQ ID NO: 20: cer sequence
SEQ ID NO: 21: psi sequence
SEQ ID NO: 22: dif sequence
SEQ ID NO: 23: cer sequence
SEQ ID NO: 24: psi sequence
SEQ ID NO: 25: Outside End(OE) sequence
SEQ ID NO: 26: DNA fragment comprising a pair of ter sequences
SEQ ID NO: 27: ori-ter cassette
SEQ ID NO: 28: ori-dif cassette
SEQ ID NO: 29: oriC transposon
SEQ ID NO: 30: loxP consensus
SEQ ID NO: 31: lox511 sequence
SEQ ID NO: 32: lox2272 sequence
SEQ ID NO: 33: loxFAS sequence
SEQ ID NO: 34: lox RE sequence
SEQ ID NO: 35: lox LE sequence
SEQ ID NO: 36: FRT sequence
SEQ ID NO: 37: rox sequence
SEQ ID NO: 38: primer SUE1156
SEQ ID NO: 39: primer SUE1361
SEQ ID NO: 40: OLDT cassette
SEQ ID NO: 41: OriC300 cassette

The invention claimed is:

1. A method for replicating circular DNA in a cell-free system, comprising the following steps:
(1) forming a reaction mixture of circular DNA as a template with a reaction solution comprising:
more than one enzyme from a first enzyme group that catalyzes replication of circular DNA, wherein the first enzyme group comprises an enzyme having DnaA activity, one or more types of nucleoid protein, an enzyme or enzyme group having DNA gyrase activity, single-strand binding protein (SSB), an enzyme having DnaB-type helicase activity, an enzyme having DNA helicase loader activity, an enzyme having DNA primase activity, an enzyme having DNA clamp activity, and an enzyme or enzyme group having DNA polymerase III* activity,
more than one enzyme from a second enzyme group that catalyzes an Okazaki fragment maturation and synthesizes two sister circular DNAs constituting a catenane, wherein the second enzyme group comprises an enzyme having DNA polymerase I activity and an enzyme having DNA ligase activity, one or more enzymes from a third enzyme group that catalyzes a separation of two sister circular DNAs, wherein the third enzyme group comprises an enzyme having topoisomerase IV activity and an enzyme having topoisomerase III activity; and a buffer, ATP, GTP, CTP, UTP, deoxyadenosine triphosphate (dATP), deoxyguanosine triphosphate (dGTP), deoxycytidine triphosphate (dCTP), and deoxythymidine triphosphate (dTTP), wherein the buffer is not water or a natural buffer; and (2) reacting the reaction mixture formed in step (1), wherein the circular DNA includes origin of chromosome (oriC) that can bind to an enzyme having DnaA activity, and further includes a pair of ter sequences that are each inserted outward with respect to oriC, and/or a nucleotide sequence recognized by a DNA multimer separation enzyme selected from a group consisting of Cre, XerCD, budding yeast (Saccharomyces verevisiae)-derived recombinant enzyme FLP, bacteriophage D6-derived recombinant enzyme DreO, Zygosaccharomyces rouxii-derived recombinant enzyme R and a serine recombinant enzyme family consisting of Gin, y $\bar{o}$, Tn3, and Hin, wherein when the circular DNA has the ter sequences, the reaction solution in step (1) further comprises a protein having an activity of inhibiting replication by binding to the ter sequences selected from a Tus protein or an RTP protein, and when the circular DNA has the nucleotide sequence recognized by the DNA multimer separation enzyme, the reaction solution in step (1) further comprises the DNA multimer separation enzyme, wherein each of the enzymes is a purified enzyme; and wherein the method does not require RNA-mediated transcription for initiation of replicating circular DNA.

2. The method according to claim 1, wherein the DNA multimer separation enzyme is Cre or XerCD.

3. The method of claim 1, wherein the pair of ter sequences that are each inserted outward with respect to oriC comprises: a sequence comprising any one of sequences shown in SEQ ID NOS: 1 to 14 which is inserted as one ter sequence into the 5'-terminal side of oriC; and a sequence comprising a complementary sequence to any one of sequences shown in SEQ ID NOS: 1 to 14 which is inserted as the other ter sequence into the 3'-terminal side of oriC.

4. The method according to claim 2, wherein the nucleotide sequence recognized by XerCD is a sequence comprising any one of sequences shown in SEQ ID NOS: 15 to 24, or a complementary sequence thereto.

5. The method according to claim 2, wherein nucleotide sequence recognized by Cre is a sequence comprising any one of sequences shown in SEQ ID NOS: 30 to 35, or a complementary sequence thereto.

6. The method of claim 1, wherein the pair of ter sequences that are each inserted outward with respect to oriC comprises: a sequence comprising any one of sequences shown in SEQ ID NOS: 1 to 14 which is inserted as one ter sequence into the 5'-terminal side of oriC; and a sequence comprising a complementary sequence to any one of sequences shown in SEQ ID NOS: 1 to 14 which is inserted as the other ter sequence into the 3'-terminal side of oriC.

7. The method of claim 1, wherein the buffer is selected from the group consisting of Tris-HCl, Hepes-KOH, a phosphate buffer, MOPS-NaOH, Tricine-HCl and Tris-acetic acid.

8. The method of claim 1, wherein the ter sequences are present in a region close to or adjacent to oriC.

* * * * *

SEQUENCE LISTING

```
<160> NUMBER OF SEQ ID NOS: 41

<210> SEQ ID NO 1
<211> LENGTH: 14
<212> TYPE: DNA
<213> ORGANISM: Artificial Sequence
<220> FEATURE:
<223> OTHER INFORMATION: ter sequence (consensus)
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (3)..(3)
<223> OTHER INFORMATION: r is a or g
<220> FEATURE:
<221> NAME/KEY: misc_feature
<222> LOCATION: (4)..(4)
<223> OTHER INFORMATION: w is a or t
<220> FEATURE:
<221> NAME/KEY: misc_feature
<222> LOCATION: (13)..(13)
<223> OTHER INFORMATION: k is g or t

<400> SEQUENCE: 1
gnrwgttgta acka                                                    14

<210> SEQ ID NO 2
```

```
<211> LENGTH: 14
<212> TYPE: DNA
<213> ORGANISM: Artificial Sequence
<220> FEATURE:
<223> OTHER INFORMATION: ter sequence (consensus)
<220> FEATURE:
<221> NAME/KEY: misc_feature
<222> LOCATION: (2)..(2)
<223> OTHER INFORMATION: k is g or t
<220> FEATURE:
<221> NAME/KEY: misc_feature
<222> LOCATION: (4)..(4)
<223> OTHER INFORMATION: w is a or t
<220> FEATURE:
<221> NAME/KEY: misc_feature
<222> LOCATION: (13)..(13)
<223> OTHER INFORMATION: k is g or t

<400> SEQUENCE: 2
gkawgttgta acka                                                  14

<210> SEQ ID NO 3
<211> LENGTH: 14
<212> TYPE: DNA
<213> ORGANISM: Artificial Sequence
<220> FEATURE:
<223> OTHER INFORMATION: ter sequence (terA, B, D, E, or H)

<400> SEQUENCE: 3
gtatgttgta acta                                                  14

<210> SEQ ID NO 4
<211> LENGTH: 18
<212> TYPE: DNA
<213> ORGANISM: Artificial Sequence
<220> FEATURE:
<223> OTHER INFORMATION: ter sequence (terA, B, D, E, or H)

<400> SEQUENCE: 4
agtatgttgt aactaaag                                              18

<210> SEQ ID NO 5
<211> LENGTH: 14
<212> TYPE: DNA
<213> ORGANISM: Artificial Sequence
<220> FEATURE:
<223> OTHER INFORMATION: ter sequence (terC)

<400> SEQUENCE: 5
ggatgttgta acta                                                  14

<210> SEQ ID NO 6
<211> LENGTH: 14
<212> TYPE: DNA
<213> ORGANISM: Artificial Sequence
<220> FEATURE:
<223> OTHER INFORMATION: ter sequence (terF)

<400> SEQUENCE: 6
gtatgttgta acga                                                  14

<210> SEQ ID NO 7
<211> LENGTH: 14
<212> TYPE: DNA
<213> ORGANISM: Artificial Sequence
<220> FEATURE:
<223> OTHER INFORMATION: ter sequence (terG)

<400> SEQUENCE: 7
```

```
ggatgttgta acta                                                    14

<210> SEQ ID NO 8
<211> LENGTH: 14
<212> TYPE: DNA
<213> ORGANISM: Artificial Sequence
<220> FEATURE:
<223> OTHER INFORMATION: ter sequence (terI)

<400> SEQUENCE: 8
ggaagttgta acga                                                    14

<210> SEQ ID NO 9
<211> LENGTH: 14
<212> TYPE: DNA
<213> ORGANISM: Artificial Sequence
<220> FEATURE:
<223> OTHER INFORMATION: ter sequence (terJ)

<400> SEQUENCE: 9
gtaagttgta acga                                                    14

<210> SEQ ID NO 10
<211> LENGTH: 23
<212> TYPE: DNA
<213> ORGANISM: Artificial Sequence
<220> FEATURE:
<223> OTHER INFORMATION: ter sequence (Bacillus, consensus)
<220> FEATURE:
<221> NAME/KEY: misc_feature
<222> LOCATION: (3)..(3)
<223> OTHER INFORMATION: w is a or t
<220> FEATURE:
<221> NAME/KEY: misc_feature
<222> LOCATION: (4)..(4)
<223> OTHER INFORMATION: r is a or g
<220> FEATURE:
<221> NAME/KEY: misc_feature
<222> LOCATION: (6)..(10)
<223> OTHER INFORMATION: n is a, c, g or t
<220> FEATURE:
<221> NAME/KEY: misc_feature
<222> LOCATION: (11)..(11)
<223> OTHER INFORMATION: y is t or c
<220> FEATURE:
<221> NAME/KEY: misc_feature
<222> LOCATION: (12)..(12)
<223> OTHER INFORMATION: n is a, c, g or t
<220> FEATURE:
<221> NAME/KEY: misc_feature
<222> LOCATION: (19)..(19)
<223> OTHER INFORMATION: n is a, c, g or t

<400> SEQUENCE: 10
acwrannnnn ynatgtacna aat                                          23

<210> SEQ ID NO 11
<211> LENGTH: 23
<212> TYPE: DNA
<213> ORGANISM: Artificial Sequence
<220> FEATURE:
<223> OTHER INFORMATION: ter sequence (Bacillus subtilis, consensus)
<220> FEATURE:
<221> NAME/KEY: misc_feature
<222> LOCATION: (8)..(8)
<223> OTHER INFORMATION: r is a or g
<220> FEATURE:
<221> NAME/KEY: misc_feature
<222> LOCATION: (10)..(10)
<223> OTHER INFORMATION: w is a or t
<220> FEATURE:
```

-continued

```
<221> NAME/KEY: misc_feature
<222> LOCATION: (12)..(12)
<223> OTHER INFORMATION: y is c or t

<400> SEQUENCE: 11
actaattraw cyatgtacta aat                                             23

<210> SEQ ID NO 12
<211> LENGTH: 28
<212> TYPE: DNA
<213> ORGANISM: Artificial Sequence
<220> FEATURE:
<223> OTHER INFORMATION: ter sequence (Bacillus subtilis, consensus)
<220> FEATURE:
<221> NAME/KEY: misc_feature
<222> LOCATION: (8)..(8)
<223> OTHER INFORMATION: r is a or g
<220> FEATURE:
<221> NAME/KEY: misc_feature
<222> LOCATION: (10)..(10)
<223> OTHER INFORMATION: w is a or t
<220> FEATURE:
<221> NAME/KEY: misc_feature
<222> LOCATION: (12)..(12)
<223> OTHER INFORMATION: y is c or t

<400> SEQUENCE: 12
actaattraw cyatgtacta aattttca                                        28

<210> SEQ ID NO 13
<211> LENGTH: 30
<212> TYPE: DNA
<213> ORGANISM: Artificial Sequence
<220> FEATURE:
<223> OTHER INFORMATION: ter sequence (terVII)

<400> SEQUENCE: 13
gaactaatta aactatgtac taaattttca                                      30

<210> SEQ ID NO 14
<211> LENGTH: 30
<212> TYPE: DNA
<213> ORGANISM: Artificial Sequence
<220> FEATURE:
<223> OTHER INFORMATION: ter sequence (terIX)

<400> SEQUENCE: 14
atactaattg atccatgtac taaattttca                                      30

<210> SEQ ID NO 15
<211> LENGTH: 28
<212> TYPE: DNA
<213> ORGANISM: Artificial Sequence
<220> FEATURE:
<223> OTHER INFORMATION: Sequence recognized by XerCD (consensus)
<220> FEATURE:
<221> NAME/KEY: misc_feature
<222> LOCATION: (7)..(7)
<223> OTHER INFORMATION: y is c or t
<220> FEATURE:
<221> NAME/KEY: misc_feature
<222> LOCATION: (8)..(8)
<223> OTHER INFORMATION: r is a or g
<220> FEATURE:
<221> NAME/KEY: misc_feature
<222> LOCATION: (9)..(9)
<223> OTHER INFORMATION: y is c or t
<220> FEATURE:
<221> NAME/KEY: misc_feature
<222> LOCATION: (12)..(17)
<223> OTHER INFORMATION: n is a, c, g or t
```

```
<220> FEATURE:
<221> NAME/KEY: misc_feature
<222> LOCATION: (23)..(23)
<223> OTHER INFORMATION: k is g or t
<220> FEATURE:
<221> NAME/KEY: misc_feature
<222> LOCATION: (28)..(28)
<223> OTHER INFORMATION: y is c or t

<400> SEQUENCE: 15
ggtgcgyrya annnnnntta tgktaaay                                              28

<210> SEQ ID NO 16
<211> LENGTH: 28
<212> TYPE: DNA
<213> ORGANISM: Artificial Sequence
<220> FEATURE:
<223> OTHER INFORMATION: Sequence recognized by XerCD (consensus, dif
      and cer)
<220> FEATURE:
<221> NAME/KEY: misc_feature
<222> LOCATION: (7)..(7)
<223> OTHER INFORMATION: y is c or t
<220> FEATURE:
<221> NAME/KEY: misc_feature
<222> LOCATION: (9)..(9)
<223> OTHER INFORMATION: y is c or t
<220> FEATURE:
<221> NAME/KEY: misc_feature
<222> LOCATION: (12)..(17)
<223> OTHER INFORMATION: n is a, c, g or t
<220> FEATURE:
<221> NAME/KEY: misc_feature
<222> LOCATION: (23)..(23)
<223> OTHER INFORMATION: k is g or t

<400> SEQUENCE: 16
ggtgcgyaya annnnnntta tgktaaat                                              28

<210> SEQ ID NO 17
<211> LENGTH: 28
<212> TYPE: DNA
<213> ORGANISM: Artificial Sequence
<220> FEATURE:
<223> OTHER INFORMATION: Sequence recognized by XerCD (consensus, dif
      and psi)
<220> FEATURE:
<221> NAME/KEY: misc_feature
<222> LOCATION: (9)..(9)
<223> OTHER INFORMATION: y is c or t
<220> FEATURE:
<221> NAME/KEY: misc_feature
<222> LOCATION: (12)..(17)
<223> OTHER INFORMATION: n is a, c, g, or t
<220> FEATURE:
<221> NAME/KEY: misc_feature
<222> LOCATION: (28)..(28)
<223> OTHER INFORMATION: y is c or t

<400> SEQUENCE: 17
ggtgcgcrya annnnnntta tgttaaay                                              28

<210> SEQ ID NO 18
<211> LENGTH: 28
<212> TYPE: DNA
<213> ORGANISM: Artificial Sequence
<220> FEATURE:
<223> OTHER INFORMATION: Sequence recognized by XerCD (consensus, cer
      and psi)
<220> FEATURE:
<221> NAME/KEY: misc_feature
<222> LOCATION: (7)..(7)
<223> OTHER INFORMATION: y is c or t
```

```
<220> FEATURE:
<221> NAME/KEY: misc_feature
<222> LOCATION: (8)..(8)
<223> OTHER INFORMATION: r is a or g
<220> FEATURE:
<221> NAME/KEY: misc_feature
<222> LOCATION: (12)..(17)
<223> OTHER INFORMATION: n is a, c, g, or t
<220> FEATURE:
<221> NAME/KEY: misc_feature
<222> LOCATION: (23)..(23)
<223> OTHER INFORMATION: k is g or t
<220> FEATURE:
<221> NAME/KEY: misc_feature
<222> LOCATION: (28)..(28)
<223> OTHER INFORMATION: y is c or t

<400> SEQUENCE: 18
ggtgcgyrca annnnnntta tgktaaay                                              28

<210> SEQ ID NO 19
<211> LENGTH: 28
<212> TYPE: DNA
<213> ORGANISM: Artificial Sequence
<220> FEATURE:
<223> OTHER INFORMATION: dif sequence
<220> FEATURE:
<221> NAME/KEY: misc_feature
<222> LOCATION: (12)..(17)
<223> OTHER INFORMATION: n is a, c, g, or t

<400> SEQUENCE: 19
ggtgcgcata annnnnntta tgttaaat                                              28

<210> SEQ ID NO 20
<211> LENGTH: 28
<212> TYPE: DNA
<213> ORGANISM: Artificial Sequence
<220> FEATURE:
<223> OTHER INFORMATION: cer sequence
<220> FEATURE:
<221> NAME/KEY: misc_feature
<222> LOCATION: (12)..(17)
<223> OTHER INFORMATION: n is a, c, g, or t

<400> SEQUENCE: 20
ggtgcgtaca annnnnntta tggtaaat                                              28

<210> SEQ ID NO 21
<211> LENGTH: 28
<212> TYPE: DNA
<213> ORGANISM: Artificial Sequence
<220> FEATURE:
<223> OTHER INFORMATION: psi sequence
<220> FEATURE:
<221> NAME/KEY: misc_feature
<222> LOCATION: (12)..(17)
<223> OTHER INFORMATION: n is a, c, g, or t

<400> SEQUENCE: 21
ggtgcgcgca annnnnntta tgttaaac                                              28

<210> SEQ ID NO 22
<211> LENGTH: 28
<212> TYPE: DNA
<213> ORGANISM: Artificial Sequence
<220> FEATURE:
<223> OTHER INFORMATION: dif sequence

<400> SEQUENCE: 22
```

```
ggtgcgcata atgtatatta tgttaaat                                         28

<210> SEQ ID NO 23
<211> LENGTH: 28
<212> TYPE: DNA
<213> ORGANISM: Artificial Sequence
<220> FEATURE:
<223> OTHER INFORMATION: cer sequence

<400> SEQUENCE: 23
ggtgcgtaca agggatgtta tggtaaat                                         28

<210> SEQ ID NO 24
<211> LENGTH: 28
<212> TYPE: DNA
<213> ORGANISM: Artificial Sequence
<220> FEATURE:
<223> OTHER INFORMATION: psi sequence

<400> SEQUENCE: 24
ggtgcgcgca agatccatta tgttaaac                                         28

<210> SEQ ID NO 25
<211> LENGTH: 19
<212> TYPE: DNA
<213> ORGANISM: Artificial Sequence
<220> FEATURE:
<223> OTHER INFORMATION: Outside End (OE) sequence

<400> SEQUENCE: 25
ctgtctctta tacacatct                                                   19

<210> SEQ ID NO 26
<211> LENGTH: 222
<212> TYPE: DNA
<213> ORGANISM: Artificial Sequence
<220> FEATURE:
<223> OTHER INFORMATION: DNA fragment containing a pair of ter sequence
<220> FEATURE:
<221> NAME/KEY: misc_feature
<222> LOCATION: (24)..(199)
<220> FEATURE:
<221> NAME/KEY: misc_feature
<222> LOCATION: (24)..(199)
<223> OTHER INFORMATION: n is a, c, g, or t

<400> SEQUENCE: 26
actttagtta caacatactt attnnnnnnn nnnnnnnnnn nnnnnnnnnn nnnnnnnnnn       60
nnnnnnnnnn nnnnnnnnnn nnnnnnnnnn nnnnnnnnnn nnnnnnnnnn nnnnnnnnnn      120
nnnnnnnnnn nnnnnnnnnn nnnnnnnnnn nnnnnnnnnn nnnnnnnnnn nnnnnnnnnn      180
nnnnnnnnnn nnnnnnnnna ataagtatgt tgtaactaaa gt                         222

<210> SEQ ID NO 27
<211> LENGTH: 383
<212> TYPE: DNA
<213> ORGANISM: Artificial Sequence
<220> FEATURE:
<223> OTHER INFORMATION: ori-ter cassette

<400> SEQUENCE: 27
agtatgttgt aactaaagat aacttcgtat aatgtatgct atacgaagtt atacagatcg       60
tgcgatctac tgtggataac tctgtcagga agcttggatc aaccggtagt tatccaaaga     120
acaactgttg ttcagttttt gagttgtgta taacccctca ttctgatccc agcttatacg    180
```

```
gtccaggatc accgatcatt cacagttaat gatcctttcc aggttgttga tcttaaaagc    240
cggatccttg ttatccacag ggcagtgcga tcctaataag agatcacaat agaacagatc    300
tctaaataaa tagatcttct ttttaatacc caggatccat ttaacataat atacattatg    360 cgcacccttta gttacaacat act                                          383

<210> SEQ ID NO 28
<211> LENGTH: 320
<212> TYPE: DNA
<213> ORGANISM: Artificial Sequence
<220> FEATURE:
<223> OTHER INFORMATION: ori-dif cassette

<400> SEQUENCE: 28
atttaacata atatacatta tgcgcaccaa gtatacagat cgtgcgatct actgtggata     60
actctgtcag gaagcttgga tcaaccggta gttatccaaa gaacaactgt tgttcagttt    120
ttgagttgtg tataaccccct cattctgatc ccagcttata cggtccagga tcaccgatca    180
ttcacagtta atgatccttt ccaggttgtt gatcttaaaa gccggatcct tgttatccac    240
agggcagtgc gatcctaata agagatcaca atagaacaga tctctaaata aatagatctt    300 cttttttaata cccaggatcc                                              320

<210> SEQ ID NO 29
<211> LENGTH: 399
<212> TYPE: DNA
<213> ORGANISM: Artificial Sequence
<220> FEATURE:
<223> OTHER INFORMATION: oriC transposon DNA

<400> SEQUENCE: 29
ctgtctctta tacacatctg aagatccggc agaagaatgg ctgggatcgt gggttaattt     60
actcaaataa gtatacagat cgtgcgatct actgtggata actctgtcag gaagcttgga    120
tcaaccggta gttatccaaa gaacaactgt tgttcagttt ttgagttgtg tataaccccct    180 cattctgatc ccagcttata cggtccagga tcaccgatca ttcacagtta atgatccttt    240
ccaggttgtt gatcttaaaa gccggatcct tgttatccac agggcagtgc gatcctaata    300
agagatcaca atagaacaga tctctaaata aatagatctt cttttttaata cccaggatcc    360 caggtctttc tcaagccgac agatgtgtat aagagacag                           399

<210> SEQ ID NO 30
<211> LENGTH: 34
<212> TYPE: DNA
<213> ORGANISM: Artificial Sequence
<220> FEATURE:
<223> OTHER INFORMATION: loxP consensus sequence

<400> SEQUENCE: 30
ataacttcgt atagcataca ttatacgaag ttat                                34

<210> SEQ ID NO 31
<211> LENGTH: 34
<212> TYPE: DNA
<213> ORGANISM: Artificial Sequence
<220> FEATURE:
<223> OTHER INFORMATION: lox 511 sequence

<400> SEQUENCE: 31
ataacttcgt atagtataca ttatacgaag ttat                                34
```

```
<210> SEQ ID NO 32
<211> LENGTH: 34
<212> TYPE: DNA
<213> ORGANISM: Artificial Sequence
<220> FEATURE:
<223> OTHER INFORMATION: lox2272 sequence

<400> SEQUENCE: 32
ataacttcgt ataggatact ttatacgaag ttat                               34

<210> SEQ ID NO 33
<211> LENGTH: 34
<212> TYPE: DNA
<213> ORGANISM: Artificial Sequence
<220> FEATURE:
<223> OTHER INFORMATION: loxFAS sequence

<400> SEQUENCE: 33
ataacttcgt atataccttt ctatacgaag ttat                               34

<210> SEQ ID NO 34
<211> LENGTH: 34
<212> TYPE: DNA
<213> ORGANISM: Artificial Sequence
<220> FEATURE:
<223> OTHER INFORMATION: lox RE sequence

<400> SEQUENCE: 34
ataacttcgt atagcataca ttatacgaac ggta                               34

<210> SEQ ID NO 35
<211> LENGTH: 34
<212> TYPE: DNA
<213> ORGANISM: Artificial Sequence
<220> FEATURE:
<223> OTHER INFORMATION: lox LE sequence

<400> SEQUENCE: 35
taccgttcgt atagcataca ttatacgaag ttat                               34

<210> SEQ ID NO 36
<211> LENGTH: 34
<212> TYPE: DNA
<213> ORGANISM: Artificial Sequence
<220> FEATURE:
<223> OTHER INFORMATION: FRT sequence

<400> SEQUENCE: 36
gaagttccta ttctctagaa agtataggaa cttc                               34

<210> SEQ ID NO 37
<211> LENGTH: 32
<212> TYPE: DNA
<213> ORGANISM: Artificial Sequence
<220> FEATURE:
<223> OTHER INFORMATION: rox sequence

<400> SEQUENCE: 37
taactttaaa taatgccaat tatttaaagt ta                                 32

<210> SEQ ID NO 38
<211> LENGTH: 19
<212> TYPE: DNA
<213> ORGANISM: Artificial Sequence
<220> FEATURE:
<223> OTHER INFORMATION: SUE1156 primer
```

```
<400> SEQUENCE: 38
ctatgcggca tcagagcag                                                    19

<210> SEQ ID NO 39
<211> LENGTH: 19
<212> TYPE: DNA
<213> ORGANISM: Artificial Sequence
<220> FEATURE:
<223> OTHER INFORMATION: SUE1361 primer

<400> SEQUENCE: 39
gttaagccag ccccgacac                                                    19

<210> SEQ ID NO 40
<211> LENGTH: 461
<212> TYPE: DNA
<213> ORGANISM: Artificial Sequence
<220> FEATURE:
<223> OTHER INFORMATION: OLDT cassette

<400> SEQUENCE: 40
cgcgtcagcg ggtgttggcg ggtgtcgggg ctggcttaac agtatgttgt aactaaagat       60
aacttcgtat aatgtatgct atacgaagtt atacagatcg tgcgatctac tgtggataac      120
tctgtcagga agcttggatc aaccggtagt tatccaaaga caactgttg ttcagttttt       180 gagttgtgta taacccctca ttctgatccc agcttatacg gtccaggatc accgatcatt     240
cacagttaat gatcctttcc aggttgttga tcttaaaagc cggatccttg ttatccacag     300
ggcagtgcga tcctaataag agatcacaat agaacagatc tctaaataaa tagatcttct    360
ttttaatacc caggatccat ttaacataat atacattatg cgcacccttta gttacaacat    420 actatgcggc atcagagcag attgtactga gagtgcacca t                          461

<210> SEQ ID NO 41
<211> LENGTH: 378
<212> TYPE: DNA
<213> ORGANISM: Artificial Sequence
<220> FEATURE:
<223> OTHER INFORMATION: OriC300 cassette

<400> SEQUENCE: 41
cgcgtcagcg ggtgttggcg ggtgtcgggg ctggcttaac agtatgttgt aactaaagat       60
ctactgtgga taactctgtc aggaagcttg gatcaaccgg tagttatcca agaacaact      120 gttgttcagt ttttgagttg tgtataaccc ctcattctga tcccagctta tacggtccag    180
gatcaccgat cattcacagt taatgatcct ttccaggttg ttgatcttaa aagccggatc    240
cttgttatcc acagggcagt gcgatcctaa taagagatca caatagaaca gatctctaaa    300
taaatagatc ttcttttaa tactttagtt acaacatact atgcggcatc agagcagatt     360
gtactgagag tgcaccat                                                    378
```